United States Patent [19]
Dervan et al.

[11] Patent Number: 5,998,140
[45] Date of Patent: Dec. 7, 1999

[54] COMPLEX FORMATION BETWEEN DSDNA AND OLIGOMER OF CYCLIC HETEROCYCLES

[75] Inventors: Peter B. Dervan, San Marino; Joel M. Gottesfeld, Del Mar, both of Calif.

[73] Assignees: The Scripps Research Institute, La Jolla; California Institute of Technology, Pasadena, both of Calif.

[21] Appl. No.: 08/853,525

[22] Filed: May 8, 1997

Related U.S. Application Data

[62] Continuation-in-part of application No. 08/837,524, Apr. 21, 1997, which is a continuation-in-part of application No. 08/607,078, filed as application No. PCT/US97/03332, Feb. 20, 1997

[60] Provisional application No. 60/023,309, Jul. 31, 1996, provisional application No. 60/024,374, Aug. 1, 1996, provisional application No. 60/026,713, Sep. 25, 1996, and provisional application No. 60/038,384, Feb. 14, 1997.

[51] Int. Cl.[6] ..................................................... C12Q 1/68
[52] U.S. Cl. .............................. 435/6; 536/24.3; 536/24.5
[58] Field of Search ................................ 435/6; 536/24.3, 536/24.5

[56] References Cited

U.S. PATENT DOCUMENTS

| | | | |
|---|---|---|---|
| 5,578,444 | 11/1996 | Edwards et al. | 435/6 |
| 5,698,674 | 12/1997 | Bruice et al. | 530/331 |

FOREIGN PATENT DOCUMENTS

| | | |
|---|---|---|
| 2005039 | of 1991 | Canada . |
| 0246868 | 11/1987 | European Pat. Off. . |
| 0388948 | 9/1990 | European Pat. Off. . |
| 2261661 | 5/1993 | United Kingdom . |
| WO 92/09574 | 6/1992 | WIPO . |
| WO 92/13838 | 8/1992 | WIPO . |
| WO 92/14707 | 9/1992 | WIPO . |
| WO 93/00446 | 1/1993 | WIPO . |
| WO 94/03434 | 2/1994 | WIPO . |
| WO 94/14980 | 7/1994 | WIPO . |
| WO 94/20463 | 9/1994 | WIPO . |
| WO 94/25436 | 11/1994 | WIPO . |
| WO 95/04732 | 2/1995 | WIPO . |
| WO 96/05196 | 2/1996 | WIPO . |
| WO 97/03957 | 2/1997 | WIPO . |
| WO 97/2812 | 8/1997 | WIPO . |
| WO 97/30975 | 8/1997 | WIPO . |

OTHER PUBLICATIONS

Ades, S.E. and Sauer, R.T. Specificity of minor–groove and major–groove interactions in a homeodomain–DNA complex. *Biochemistry* 34: 14601–14608 (1995).

Al–Said, N. and Lown, J.W. Synthesis of novel cross–linked bis–lexitropsins. *Tet Lett.* 35: 7577–7580 (1994).

Baird, E.E and Dervan, P.B. Solid phase synthesis of polyamides containing imidazole and pyrrole amino acids. *J. Am. Chem. Soc.* 118: 6141–6146 (1996).

Breslauer, K.J. et al. The origins of the DNA binding affinity and specificity of minor groove directed ligands: Correlations of thermodynamic and structural data. *Structure & Expression* 2: 273–290 (1988).

Bruice, T.C. et al. Rational design of substituted tripyrrole peptides that complex with DNA by both selective minor–groove binding and electrostatic interaction with the phosphate backbone. *Proc. Natl. Acad. Sci. USA* 89: 1700–1704 (1992).

Bruice, T.C. et al. A microgonotropen branched decaaza decabutylamine and its DNA and DNA/transcription factor interactions. *Bioorg. Med. Chem.* 5: 685–692 (1997).

Chen, X. et al. Binding of two distamycin A molecules in the minor groove of an alternating B–DNA duplex. *Nature Struct. Biol.* 1: 169–175 (1994).

Chen, X. et al. Crystal structure of the side–by–side binding of distamycin to AT–containing DNA octamers d(ICITACIC) and d(ICATATIC). *J. Mol. Biol.* 267: 1157–1170 (1997).

Chen, Y.H. and Lown, J. W. A new DNA minor groove binding motif: cross–linked lexitropsins. *J. Am. Chen. Soc.* 116: 6995–7005 (1994).

Chiang, S–Y. et al. Targeting E2F1–DNA complexes with microgonotropen DNA binding agents. *Proc. Natl. Acad. Sci. USA* 94: 2811–2816 (1997).

Cho, J. et al. Cyclic polyamides for recognition in the minor groove of DNA, *Proc. Natl. Acad. Sci. USA* 92: 10389–10392 (1995).

Church, K.M. et al. N–(2–chloroethyl)–N–nitrosoureas covalently bound to nonionic and monocationic lexitropsin dipeptides. Synthesis, DNA affinity binding characteristics, and reactions with [32]p–end–labeled DNA. *Biochemistry* 29: 6827–6838 (1990).

Dale, J.A. and Mosher, H.S. Nuclear magnetic resonance enantiomer reagents. Configurational correlations via nuclear magnetic resonance chemical shifts of diastereomeric mandelate, O–methylmandelate, and α–methoxy–α–trifluoromethylphenylacetate (MTPA) Esters[1,2]. *J. Am. Chen. Soc.* 95: 512–519 (1973).

de Clairac, R.P.L. et al. NMR characterization of hairpin polyamide complexes with the minor groove of DNA. *J. Am. Chem. Soc..* 119: 7909–7916 (1997).

Dervan, P.B. Design of sequence–specific DNA–binding molecules. *Science* 232: 464–471 (1997).

(List continued on next page.)

*Primary Examiner*—Scott W. Houtteman
*Attorney, Agent, or Firm*—Morrison & Foerster, LLP

[57] ABSTRACT

Methods and compositions are provided for forming complexes intracellularly between dsDNA and oligomers of heterocycles, aliphatic amino acids, particularly omega-amino acids, and a polar end group. By appropriate choice of target sequences and composition of the oligomers, complexes are obtained with low dissociation constants. The formation of complexes can be used for modifying the phenotype of cells, either prokaryotic or eukaryotic, for research and therapy.

53 Claims, 4 Drawing Sheets

OTHER PUBLICATIONS

Duval–Valentin, G. et al. Specific inhibition of transcription by triple helix–forming oligonucleotides. *Proc. Natl. Acad. Sci. USA* 89: 504–508 (1992).

Dwyer, T.J. et al. Design and binding of a distamycin A analog to d(CGCAAGTTGGC)•d(GCCAACTTGCG): Synthesis NMR studies, and implications for the design of sequence–specific minor groove binding oligopeptides. *J. Am. Chem. Soc.* 114: 5911–5919 (1992).

Dwyer, T.J. et al. Structural analysis of covalent peptide dimers, bis(pyridine–2–carboxamidonetropsin) $(CH_2)_{3-6}$, in complex with 5'-TGACT-3' sites by two–dimensional NMR. *J. Am. Chem. Soc.* 115: 9900–9906 (1993).

Feng, et al. *Science* 263: 348–355 (1994).

Gartenberg, M.R. and Crothers, D.M. DNA sequences determinants of CAP–induced bending and protein binding affinity. *Nature* 333: 824–829 (1988).

Geierstanger, B.H. et al. NMR characterization of a heterocomplex formed by distamycin and its analog 2–ImD with d(CGCAAGTTGGC):d(GCCAACTTGCG): Preference for the 1:1:1 2–ImD:Dst:DNA complex over the 2:1 2–ImD:DNA and the 2:1 Dst:DNA complexes. *J. Am. Chem.* 115: 4474–4482 (1993).

Geierstanger, B.H. et al. Design of a G•C–specific DNA minor groove–binding peptide. *Science* 266: 646–650 (1994).

Geierstanger, B.H. et al. Extending the recognition site of designed minor groove binding molecules. *Nature Struct. Biol.* 3: 321–324 (1996).

Gottesfeld, J.M. et al. Regulation of gene expression by small molecules. *Nature* 387: 202–205 (1997).

He, G.–H. et al. Microgonotropens and their interactions with DNA. $1.^1$ synthesis of the tripyrrole peptides dien–microgonotropen–a,–b, and –c and characterization of their interactions with dsDNA. *J. Am. Chen. Soc.* 115: 7061–7071 (1993).

Herman, D.M. et al. Stereochemical control of the DNA binding affinity, sequence specificity, and orientation preference of chiral hairpin polyamides in the minor groove. *J. Am. Chem. Soc.* 120: 1382–1391 (1998).

Ho, S.N. et al. Specific inhibition of formation of transcription complexes by a calicheamicin oligosaccharide: a paradigm for the development of transcriptional antagonists. *Proc. Natl. Acad. Sci. USA* 91: 9203–9207 (1994).

Hyde, C. et al. Some 'difficult sequences' made easy—A study of interchain association in solid–phase peptide synthesis. *Int. J. Peptide Protein Res.* 43: 431–440 (1994).

Kelly, J.J. et al. Binding site size limit of the 2:1 pyrrole––imidazole polyamide–DNA motif. *Proc. Natl. Acad. Sci. USA* 93: 6981–6985 (1996).

Kent, S.B.H. Chemical Synthesis of peptides and proteins. *Annu. Rev. Biochem.* 57: 957–989 (1988).

Kielkopf, C.L. et al. Structural basis for G•C recognition in the DNA minor groove. *Nature Struct. Biol.* 5: 104–109 (1998).

Kim, Y. et al. Crystal structure of a yeast TBP/TATA–box complex. *Nature* 365:512–520 (1993).

Kopka, M.L. et al. Defining GC–specificity in the minor groove: side–by–side binding of the di–imidazole lexitropsin to C–A–T–G–G–C–C–A–T–G. *Structure* 5: 1033–1046 (1997).

Lee, M. et al. Structural and dynamic aspects of binding of a prototype lexitropsion to the decadeoxyribonucleotide $d(CGCAATTGCG)_2$ deduced from high–resolution $^1H$ NMR studies. *Biochemistry* 27:445–455 (1988).

Liu, C. et al. Sequence–selective carbohydrate–DNA interaction: dimeric and monomeric forms of the calilcheamicin oligosaccharide interfere with transcription factor function. *Proc. Natl. Acad. USA* 93: 940–944 (1996).

Maher, L.J. et al. Analysis of promoter–specific repression by triple–helical DNA complexes in a eukaryotic cell–free transcription system. *Biochemistry* 31: 70–81 (1992).

Moser, H.E. and Dervan, P.B. Sequence–specific cleavage of double helical DNA by triple helix formation. *Science* 238: 645–650 (1987).

Mrksich, M. et al. Antiparallel side–by–side dimeric motif for sequence–specific recognition in the minor groove of DNA by the designed peptide 1–methylimidazole–2–carboxamide netropsin. *Proc. Natl. Acad. Sci. USA* 89: 7586–7590 (1992).

Mrksich, M. and Dervan, P.B. Enhanced sequence specific recognition in the minor groove of DNA by covalent peptide dimers: Bis(pyridine–2–carboxamidonetropsin) $(CH_2)_{3-6}$. *J. Am. Chem. Soc.* 115: 9892–9899 (1993).

Mrksich, M. and Dervan, P.B. Antiparallel side–by–side heterodimer for sequence–specific recognition in the minor groove of DNA by a distamycin/1–methylimidazole–2–carboxamide–netropsin pair. *J. Am. Chem. Soc.* 115: 2572–2576 (1993).

Mrksich, M. and Dervan, P.B. Design of a covalent peptide heterodimer for sequence–specific recognition in the minor groove of double–helical DNA. *J. Am. Chem. Soc.* 116: 3663–3664 (1994).

Mrksich, M. et al. Hairpin peptide motif. A new class of oligopeptides for sequence–specific recognition in the minor groove of double–helical DNA. *J. Am. Chem. Soc.* 116: 7983–7988 (1994).

Mrksich, M. and Dervan, P.B. Recognition in the minor groove of DNA at 5'-(A,T)GCGC(A,T)-3' by a four ring tripeptide dimer. Reversal of the specificity of the natural product distamycin. *J. Am. Chem. Soc.* 117: 3325–3332 (1995).

Neely, L. et al. Importance of minor groove binding zinc fingers within the transcription factor IIIA–DNA complex. *J. Mol. Biol.* 274: 439–445 (1997).

Nielsen, P.E. Design of sequence–specific DNA binding ligands. *Chem. Eur. J.* 3: 505–508 (1997).

Nishiwaki, E. et al. Efficient synthesis of oligo–n–methylpyrrolecarboxamides and related compounds. *Heterocycles* 27: 1945–1952 (1988).

Oakley, M.G. et al. Evidence that a minor groove–binding peptide and a major groove–binding protein can simultaneously occupy a common site on DNA. *Biochemistry* 31: 10969–10975 (1992).

Parks, M.E. et al. Recognition of 5'-(A,T)GG(A,T)-3' sequences in the minor groove of DNA by hairpin polyamides. *J. Am. Chem. Soc.* 118: 6153–6159 (1996).

Parks, M.E. et al. Optimization of the hairpin polyamide design for recognition of the minor groove of DNA. *J. Am. Chem. Soc.* 118: 6147–6152 (1996).

Pelton, J.G. and Wemmer, D.E. Structural characterization of a 2:1 distamycin A•d(CGCAAATTGGC) complex by two–dimensional NMR. *Proc. Natl. Acad. Sci. USA* 86: 5723–5727 (1989).

Pelton, J.G. and Wemmer, D.E. Binding modes of distamycin A with d(CGCAAATTTGCG)$_2$ determined by two–dimensional NMR. *J. Am. Chem. Soc.* 112: 1393–1399 (1990).

Pilch, D.S. et al. Binding of a hairpin polyamide in the minor groove of DNA: sequence–specific enthalpic discrimination. *Proc. Natl. Acad. Sci. USA* 93: 8306–8311 (1996).

Pullman, B. Molecular mechanisms of specificity in DNA—Antitumor drug interactions. *Adv. Drug. Res.* 18: 1–113 (1989).

Seeman, N.C. et al. Sequence–specific recognition of double helical nucleic acids by proteins. *Proc. Natl. Acad. Sci. USA* 73: 804–808 (1976).

Singh, S.B. et al. Relative binding affinities of distamycin and its analog to d(CGCAAGTTGGC)•d(GCCAACTTGCG): Comparison of simultation results with experiment. *Proc. Natl. Acad. Sci. USA* 91: 7673–7677 (1994).

Sluka, J.P. et al. Importance of minor–groove contacts for recognition of DNA by the binding domain of Hin recombinase. *Biochemistry* 29: 6551–6561 (1990).

Steitz, T.A. Sructural studies of protein–nucleic acid interaction: the sources of sequence–specific binding. *Quart. Rev. Biophys.* 23: 205–280 (1990).

Swalley, S.E. et al. Recognition of a 5'–(A,T)GGG(A,T)$_2$–3' sequence in the minor groove of DNA by an eight–ring hairpin polyamide. *J. Am. Chem. Soc.* 118: 8198–8206 (1996).

Swalley, S.E. et al. Discrimination of 5'–GGGG–3', 5'–GCGC–3', and 5'–GGCC–3' sequences in the minor groove of DNA by eight–ring hairpin polyamides. *J. Am. Chem. Soc.* 119: 6953–6961 (1997).

Swalley, S.E. et al. A pyrrole–imidazole polyamide motif for recognition of eleven base pair sequences in the minor groove of DNA. *Chem. Eur. J.* 3: 1600–1607 (1997).

Szewczyk, J.W. et al. Cooperative triple–helix formation via a minor groove dimerization domain. *J. Am. Chem. Soc.* 118: 6778–6779 (1996).

Szewczyk, J.W. et al. Sequence–specific recognition of DNA by a major and minor groove binding ligand. *Angew. Chem. Int. Ed. Engl.* 35: 1487–1489 (1996).

Taylor, J.S. et al. DNA affinity cleaving. Sequence specific cleavage of DNA by distamycin–EDTA • Fe(II) and EDTA–distamycin • Fe(II). *Tetrahedron* 40: 457–465 (1984).

Thuong, N.T. and Helene, C. Sequence–specific recognition and modification of double–helical DNA by oligonucleotides. *Angew. Chem. Int. Ed. Engl.* 32: 666–690 (1993).

Trauger, J.W. et al. Recognition of DNA by designed ligands at subnanomolar concentrations. *Nature* 382: 559–561 (1996).

Trauger, J.W. et al. Extension of sequence–specific recognition in the minor groove of DNA by pyrrole–imidazole polyamides to 9–13 base pairs. *J. Am. Chem. Soc.* 118: 6160–6166 (1996).

Trauger, J.W. et al. Extended hairpin polyamide motif for sequence–specific recognition in the minor groove of DNA. *Chem. & Biol.* 3: 369–377 (1996).

Turner, J.M. et al. Recognition of seven base pair sequences in the minor groove of DNA by ten–ring pyrrole–imidazole polyamide hairpins. *J. Am. Chem. Soc.* 119: 7636–7644 (1997).

Van Dyke, M.W. et al. Map of distamycin, netropsin, and actinomycin binding sites on hetergeneous DNA: DNA cleavage–inhibition patterns with methidiumpropyl–EDTA•Fe(II). *Proc. Natl. Acad. Sci. USA* 79: 5470–5474 (1982).

Van Dyke, M.W. and Dervan, P.B. Echinomycin binding sites on DNA. *Science* 225: 1122–1127 (1984).

Wade, W.S. et al. Design of peptides that bind in the minor groove of DNA at 5'–(A,T)G(A,T)C(A,T)–3' sequences by a dimeric side–by–side motif. *J. Am. Chem. Soc.* 114: 8783–8794 (1992).

Wade, W.S. et al. Binding affinities of synthetic peptides, pyridine–2–carboxamidonetropsin and 1–methylimidazole–2–carboxamidonetropsin, that form 2:1 complexes in the minor groove of double–helical DNA. *Biochemistry* 32: 11385–11389 (1993).

Walker, W.L. et al. Estimation of the DNA sequence discriminatory ability of hairpin–linked lexitropsins. *Proc. Natl. Acad. Sci. USA* 94: 5634–5639 (1997).

Wemmer, D.E. and Dervan, P.B. Targeting the minor groove of DNA. *Curr. Opin. Struct. Biol.* 7: 355–361 (1997).

White, S. et al. Effects of the A•T/T•A degeneracy of pyrrole–imidazole polyamide recognition in the minor groove of DNA. *Biochemistry* 35: 12532–12537 (1996).

White, S. et al. On the pairing rules for recognition in the minor groove of DNA by pyrrole–imidazole polyamides. *Chem & Biol.* 4: 569–578 (1997).

White, S. et al. Orientation preferences of pyrrole–imidazole polyamides in the minor groove of DNA. *J. Am. Chem. Soc.* 119: 8756–8765 (1997).

White, S. et al. Recognition of the four Watson–Crick base pairs in the DNA minor groove by synthetic ligands. *Nature* 391: 468–470 (1998).

Wong, J.M. and Bateman, E. TBP—DNA interactions in the minor groove discriminate between A:T and T:A base pairs. *Nucl. Acids Res.* 22: 1890–1896 (1994).

Yamaguchi, S. Nuclear magnetic resonance analysis using chiral derivatives. *Asymmetric Synthesis* 1: 125–152 (1983).

Zimmer, C. and Wahnert, A. Nonintercalating DNA–binding ligands: specificity of the interaction and their use as tools in biophysical, biochemical, and biological investigations of the genetic material. *Prog. Biophys. Molec. Biol.* 47: 31–112 (1986).

Youngquist, R. Scott and Dervan, Peter B., A Synthetic Peptide Binds 16 BAse pairs of A,T Double Helical DNA, *J. American Chemical Society*, vol. 109, No. 24, 1987 pp. 7564–7566.

Goodchild, Bioconjugate Chemistry, 1(3):165–187, May, 1990.

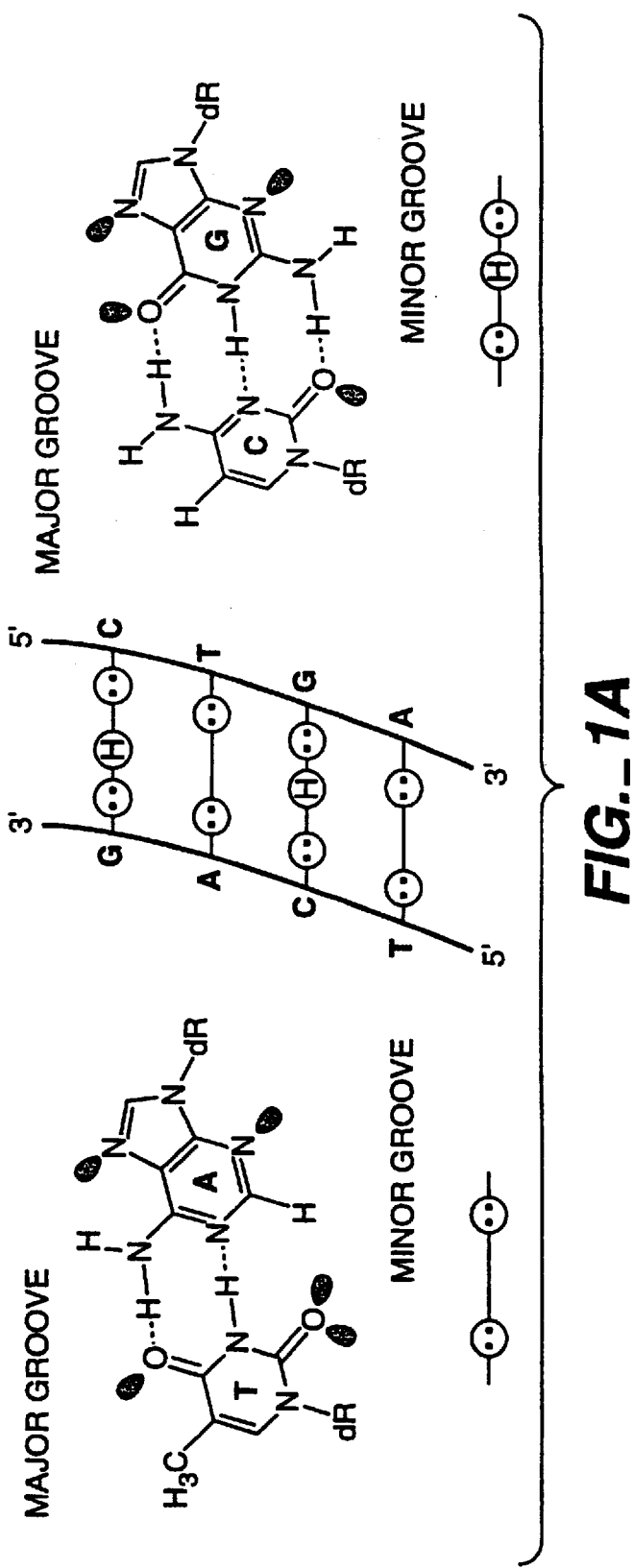
FIG._1A

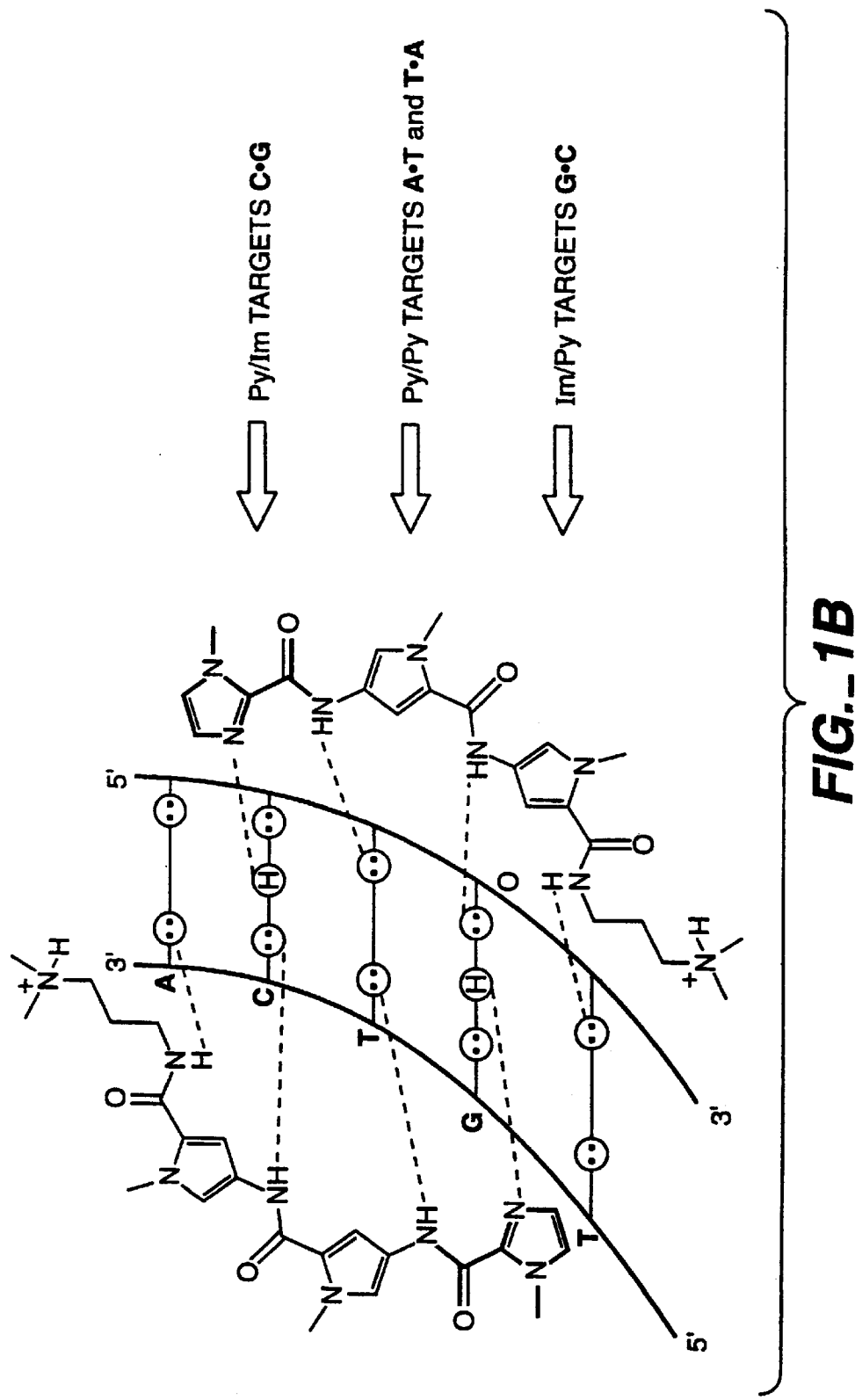
FIG._1B

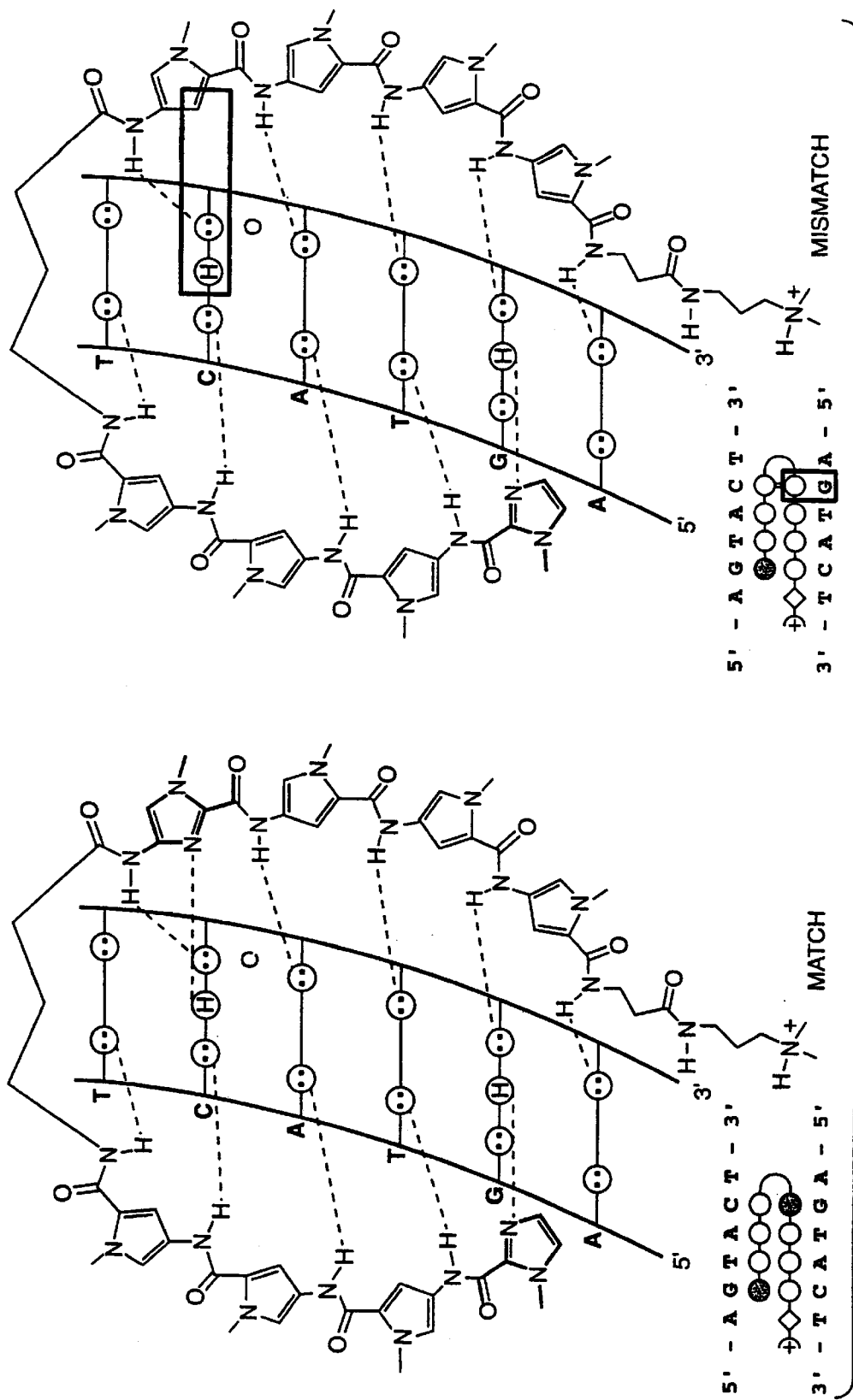
FIG._2A

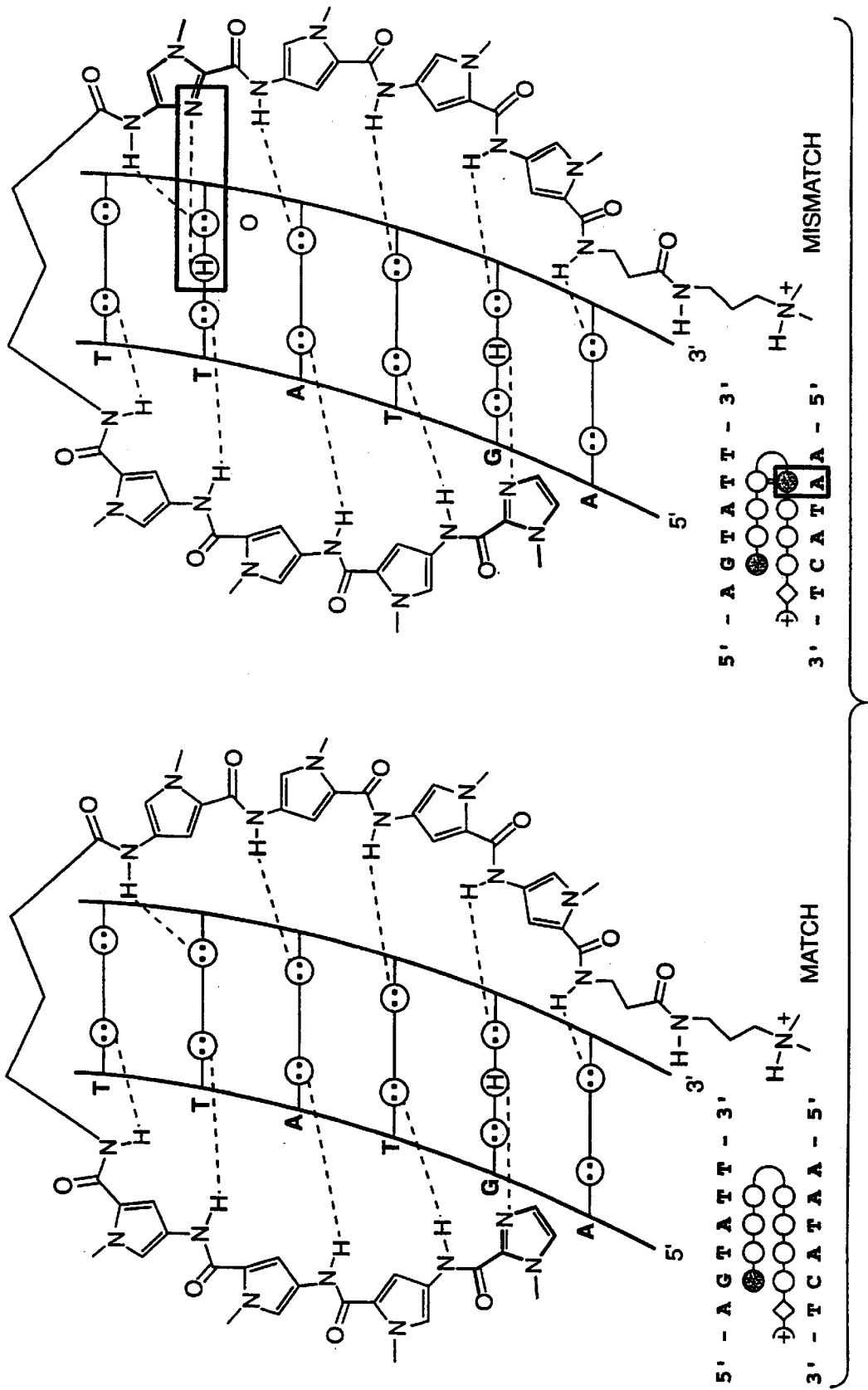
FIG._2B

COMPLEX FORMATION BETWEEN DSDNA AND OLIGOMER OF CYCLIC HETEROCYCLES

CROSS REFERENCE TO RELATED APPLICATIONS

This application is a continuation in part of application Ser. No. 08/837,524, filed 21 Apr. 1997, which is a continuation-in-part of application Ser. No. 08/607,078, filed 26 Feb. 1996 and filed as PCT/US97/03332 on 20 Feb. 1997; and claims the benefit of U.S. Provisional Applications 60/023,309, filed 31 Jul. 1996, 60/024,374, filed 01 Aug. 1996, 60/026,713, filed 25 Sep. 1996, and 60/038,384 filed 14 Feb. 1997.

The U.S. Government has certain rights in this invention pursuant to Grant Nos. GM 26453, 27681 and 47530 awarded by the National Institute of Health.

INTRODUCTION

Background

With the explosion of techniques for the synthesis, analysis and manipulation of nucleic acids, numerous new opportunities have arisen in diagnostics and therapeutics. In research there is substantial interest in being able to identify DNA sequences, which may be associated with specific organisms, alleles, mutations, and the like, to understand particular genetic processes, to identify diseases, for forensic medicine, etc. Also, for many purposes, one may wish to modulate the activity of a particular gene, so as to identify the function of a particular gene, the effect of changes in its cellular concentration on the function of the cell, or other cellular characteristic. In therapeutics, one may wish to inhibit the proliferation of cells, such as bacterial, fungal and chlamydia cells, which may act as pathogens, of viruses, of mammalian cells, where proliferation results in adverse effects on the host, or other situation. In vivo, one may provide for reversible or irreversible knock out, so that information can be developed on the development of a fetus, or the effect on the organism of reduced levels of one or more genetic products.

In a number of seminal papers, Peter Dervan's group has shown that oligomers of nitrogen heterocycles can be used to bind to dsDNA. It has been shown that there is specificity in that G/C is complemented by N-methyl imidazole (Im)/N-methyl pyrrole (Py), C/G is complemented by Py/Im, A/T and T/A are redundantly complemented by Py/Py. In effect, N-methyl imidazole tends to be associated with guanosine, while N-methyl pyrrole is associated with cytosine, adenine, and thymidine. By providing for two chains of the heterocycles, as 1 or 2 molecules, a 2:1 complex with dsDNA is formed, with the two chains of the oligomer antiparallel, where G/C pairs have Im/Py in juxtaposition, C/G pairs have Py/Im, and T/A pairs have Py/Py in juxtaposition. The heterocycle oligomers are joined by amide carbamyl) groups, where the NH may participate in hydrogen bonding with nitrogen unpaired electrons, particularly of adenine. While the complexes were of substantial interest, the binding affinities for the most part were less than about $10^6$ $M^{-1}$. Furthermore, the discrimination between a target DNA sequence, and one involving a mismatch was frequently not better than about two-fold. Therefore, for many purposes, the complexes had limited utility.

Improvements in affinity were shown for a cyclic dimer, where the two oligomers were joined at their ends by γ-aminobutyric acid, where the affinity was shown to be enhanced to about $10^9$ $M^{-1}$. However, the difference in affinity between the target sequence and single-base mismatch sequences were less than three-fold difference for three different single-base mismatch sequences. This would severely limit the applications for the compound in the presence of a large amount of naturally occurring dsDNA.

Also, for many applications, one wishes to be able to use the sequences with viable cells. There was no showing that these oligomers would be capable of being transported across a cellular membrane to the nucleus and, upon successful transport to the nucleus, they could bind to the chromosomal DNA, where the chromosomal DNA is present as nucleosomes.

Relevant Literature

Wade et al., J.AM.CHEM.SOC., 1992, 114, 8783–8794; Mrkish et al., PROC.NATL.ACAD.SCI. USA, 1992, 89, 78567590; Mrkish and Dervan, J.AM.CHEM.SOC., 1993, 115, 2572–2576; Wade et al., Biochemistry, 1993, 32, 11385–11389; Mrkish and Dervan, J.AM.CHEM.SOC., 1993, 115, 9892–9899; Dwyer et al., J.AM.CHEM.SOC., 1993, 115, 9900–9906; Mrkish and Dervan, J.AM.CHEM.SOC., 1994, 116, 3663–3664; Mrkish et al, J.AM.CHEM.SOC., 1994, 116, 7983–7988; Mrkish and Dervan J.AM.CHEM.SOC., 1995, 117, 3325–3332; Cho et al., PROC.NATL.ACAD.SCI. USA, 1995, 92, 10389–10392; Geierstanger, Nature Structural Biology, 1996, 3, 321–324; Parks et al., J.AM.CHEM.SOC., 1996, 118, 6147–6152; Parks et al., J.AM.CHEM.SOC., 1996, 118, 6153–6159; Baird and Dervan, J.AM.CHEM.SOC., 1996, 118, 6141–6146; Swalley et al., J.AM.CHEM.SOC., 1996, 118, 8198–8206; Trauger et al., J.AM.CHEM.SOC., 1996, 118, 6160–6166; Szewczyk et al., J.AM.CHEM.SOC., 1996, 118, 6778–6779; Trauger et al., Chemistry & Biology, 1996, 3, 369–377; Trauger et al., Nature, 1996, 382, 559–561; Kelly et al., PROC.NATL.ACAD.SCI. USA, 1996, 93, 6981–6985; Szewczyk et al., ANGEW.CHEM.INT.ED.ENGL., 1996, 35, 1487–1489; Pilch et al., PROC.NATL.ACAD.SCI. USA, 1996, 93, 8306–8311; White et al., Biochemistry, 1996, 35, 12532–12537.

SUMMARY OF THE INVENTION

Methods and compositions are provided for selectively producing a complex intracellularly at low concentrations, between dsDNA and an oligomer of organic cyclic groups, wherein at least 60% of the cyclic groups are heterocyclics, and at least 60% of the heterocycles have at least one nitrogen annular member. The heterocycles form complementary pairs, where at least two of the nucleotide pairs are preferentially paired with a specific pair of heterocycles. There are at least three complementary pairs of organic cyclic groups in the complex, either as a result of a hairpin turn in a single oligomer, or the complementation between organic cyclic groups of two oligomeric molecules. Usually, a small aliphatic amino acid will be interspersed in or divide what would otherwise be a chain of six or more consecutive organic cyclic groups. To further enhance binding, a terminus may have at least one aliphatic amino acid of from two to six carbon atoms and/or an alkyl chain having a polar group proximal to the linkage of the alkyl chain. By appropriate selection of the target sequence, the complementary pairs, unpaired organic cyclic groups, the aliphatic amino acids, and the polar-substituted alkyl chain, complexes may be formed with high affinity, low dissociation constants, and significant disparities in affinity between the target sequence and single-base mismatches. Modifications of the oligomers are used to provide for specific properties and are permitted at sites which do not significantly interfere with the oligomers positioning in the minor groove. The compositions are found to be able to enter viable cells and inhibit transcription of genes comprising the target sequence, cleave at particular sites, become covalently bonded at specific sites, direct selected molecules to a target site, as well as perform other activities of interest.

The oligomers are combined with cells in culture, in vivo and ex vivo under conditions where the oligomers are transported across the cell membrane to the nucleus, where the oligomers bind to the dsDNA with high affinity. Binding of the oligomers with inhibition of transcription can be used in research, modification of phenotype for change in characteristics of a host, for example, in animal husbandry and breeding, in prophylactic and therapeutic treatment, and the like.

BRIEF DESCRIPTION OF THE DRAWINGS

FIGS. 1(a)–1(c) illustrate the nine zinc finger protein TFIIIA with the 5S RNA gene internal control region (ICR). (middle) Sequence of the ICR recognized by zinc finger 4 in the minor groove. (right) Complex of hairpin polyamide 1 with its target site, 5'-AGTACT-3'. Circles with dots represent lone pairs on N3 of purines and O2 of pyrimidines. Circles containing an H represent the N2 hydrogen of guanine. (b) Structures of polyamides ImPyPyPy-γ-ImPyPy Py-β-Dp (1), ImPyPyPy-γ-PyPyPyPy-β-Dp (2), and ImPyImPy-γ-PyPyPyPy-β-Dp (3). (γ=γ-aminobutyric acid; β=β-aminoalanine; Dp=dimethylaminopropylamide).

FIGS. 2(a)–2(b) depicts binding models for (a) 5'-AGTACT-3' in complex with polyamides 1 (match) and 2 (mismatch), and (b) S'-AGTATT-3' in complex with polyamides 2 (match) and 1 (mismatch). Circles with dots represent lone pairs on N3 of purines and O2 of pyrimidines, and circles containing an H represent the N2 hydrogen of guanine. Putative hydrogen bonds are illustrated by dashed lines. The dark and open circles represent imidazole and pyrrole rings, respectively, the curved line represents γ-aminobutyric acid, and the diamond represents β-alanine. Single hydrogen bond mismatches are highlighted.

DESCRIPTION OF THE SPECIFIC EMBODIMENTS

The subject invention provides novel oligomers for forming high affinity complexes with dsDNA. The oligomers comprise organic cyclic groups joined together by short linkers, which oligomers fit in the minor groove of dsDNA and form complementary pairs with specific nucleotide base pairs in the dsDNA target sequence. Associated with the organic cyclic compounds are aliphatic amino acids, particularly aliphatic amino acids having a terminal amino group. In addition, a terminus will desirably have a polar group, conveniently substituted on an alkyl substituent. There will be a consecutive series of at least three complementary pairs of organic heterocycles, where by complementary is intended a preferential juxtaposition with a complementary pair of nucleotides. By appropriate selection of complementary pairs, unpaired organic cyclic compounds in juxtaposition to particular nucleotides of base pairs, aliphatic amino acids, and a polar group substituent, high affinities and high specificities as compared to single-base mismatches can be achieved. The subject compositions are shown to be capable of being transported across cellular membranes to the nucleus, binding to chromosomal DNA, and fulfilling a variety of intracellular functions, including inhibiting transcription. The compositions may be modified to be used in diagnostics, particularly by providing for detectable labels, or may be used in research or therapeutics, to inhibit transcription of target genes. The compositions may be otherwise modified to enhance properties for specific applications, such as transport across cell walls, association with specific cell types, cleaving of nucleic acids at specific sites, change chemical and physical characteristics, and the like.

The oligomers of the subject invention will have at least six organic heterocyclic groups, more usually at least seven, and may have eight or more, usually not more than about thirty, more usually not more than about twenty, frequently not more than about 18, organic cyclic groups, wherein at least 60%, preferably at least 80%, and more preferably at least 100% are heterocycles. The heterocycles generally have from one to three, more usually from one to two heteroatoms, where the heteroatoms are nitrogen, oxygen and sulphur, particularly nitrogen. The nitrogen atoms may be substituted, depending upon whether the nitrogen atom is directed toward the floor or surface of the groove or away from the groove. Greater latitude in the nature of the substitution is permitted when the nitrogen atom is directed away from the floor of the groove. The orientation of the oligomer is preferably N to C in association with the 5' to 3' direction of the strand to which it is juxtaposed.

The heterocycles may be substituted at positions of the heterocycle which are directed away from the floor of the groove for any purpose. Thus, a hydrogen atom may be substituted with a substituent of interest, where the substituent will not result in steric interference with the wall of the minor groove or otherwise create repulsion. When substituted, the substituents may be widely varied, being heteroatom, hydrocarbyl of from 1 to 30, more usually 1 to 20, carbon atoms, particularly 1 to 10, more particularly 1 to 6 carbon atoms, including aliphatic, alicyclic, aromatic, and combinations thereof, including both aliphatically saturated and unsaturated, having not more than 10% of the carbon atoms participating in aliphatic unsaturation, heterosubstituted hydrocarbyl (as defined previously), having from 1 to 10, usually 1 to 8, more usually 1 to 6, heteroatoms, including aliphatic, alicyclic, aromatic and heterocyclic, and combinations thereof, where the heteroatoms are exemplified by halogen, nitrogen, oxygen, sulfur, phosphorous, metal atoms, boron, arsenic, selenium, rare earths, and the like, wherein functional groups are exemplified by amino, including mono- and disubstituted amino, oxy, including hydroxy and oxyether, thio, including mercapto and thioether, oxo, including oxo-carbonyl (aldehyde and ketone) and non-oxo-carbonyl (carboxy, including acyl halide, anhydride, ester, and amide), phosphorous, including phosphines, phosphites, phosphates, phosphoramidites, etc., boron, including borates, borinic acids and borinates, nitro, cyano, azo, azoxy, hydrazino, etc.

The functional groups may be bonded to an annular member or to a substituent bonded to an annular member, e.g. carboxyalkyl, methoxyethyl, methoxymethyl, aminoethyl, dialkylaminopropyl, polyoxyethylene, polyaminoethylene, etc. In many cases, for annular nitrogen substituents, conveniently, they will be substituted with an alkyl group of from 1 to 3 carbon atoms, particularly methyl, and at least one adjacent annular carbon atom unsubstituted. For the most part, individual substituents will be under 600 Dal, usually under about 300 Dal, and preferably under about 150 Dal and the total for substituents bonded to annular members will be under about 5 kDal, usually under about 2 kDal, more usually under about 1 kDal, there generally being from about 0 to 5, more usually from about 0 to 3 substituents, for other than the alkyl of from 1 to 3 carbon atoms bonded to annular nitrogen. Generally, the total carbon atoms for the substituents will not be greater than about 100, usually not greater than about 60 more usually not greater than about 30, with not more than 30 heteroatoms, usually not more than 20 heteroatoms, more usually not more than about 10 heteroatoms.

The heterocycles will normally be linked at the 2 position and the 4 or 5 position, particularly the 2 and 4 position for 5 annular member rings.

The heterocycles are five to six annular members, particularly five annular members, having from one to three, usually one to two heteroatoms, where two heteroatoms are usually spaced apart by at least one intervening carbon atom. The organic cyclic groups are completely unsaturated and will be referred to as aromatic as that term is understood for organic cyclic compounds of from five to six annular members.

Illustrative annular members include pyrrole, imidazole, triazole, furan, thiophene, oxazole, thiazole, pyrazole, cyclopentadiene, pyridine, pyrimidine, triazine, and the like, where as indicated above, NH groups in the rings when substituted are preferably alkylated with an alkyl group of from one to three carbon atoms, particularly methyl. The preferred organic cyclic compounds are five membered rings having from one to two nitrogen atoms, where one of the nitrogen atoms is methylated.

The linking groups between the organic cyclic groups will generally have a length of two atoms, wherein at least some of the lining groups will have NH, where the NH may hydrogen bond with an unshared pair of electrons of the nucleotides. The linking chains may be methyleneamino, carbamyl (—CONH—), ethylene, thiocarbamyl, imidinyl, and the like, particularly carbamyl and its heteroanalogs, e.g. thio and imino.

In addition to the organic cyclic compounds, aliphatic amino acids are employed, particularly ω-amino aliphatic amino acids, either to provide for hairpin turns to provide complementation between two sequences of heterocycles, to form a cyclic compound where the oligomers are joined at both ends, or to provide for a shift in spacing of the organic cyclic compounds in relation to the target dsDNA. For the most part, the aliphatic amino acids will have a chain as a core structure of two to six carbon atoms, usually of two to four carbon atoms, desirably having terminal amino groups, particularly glycine, β-alanine, and γ-aminobutyric acid, being unsubstituted or substituted on carbon and nitrogen, particularly carbon, although for the most part the aliphatic amino acids will be unsubstituted. The substituents have been described previously. Where an aliphatic amino acid is C-terminal, the carboxyl group will usually be functionalized as an ester or amide, where the alcohol or amino acid may be selected to provide for specific properties or be used to reduce the charge of the carboxyl group. For the latter, the alcohol and amino groups will generally be from 0 to 6 carbon atoms, usually from 0 to 3 carbon atoms.

As indicated above, these amino acids will play specific roles. The longer chain aliphatic amino acid will serve to provide for turns in the molecule and to close the molecule to form a ring. The shorter chain aliphatic amino acids will be employed, both to provide a shift for spacing in relation to the target dsDNA, and to provide enhanced binding by being present proximal to the terminal organic cyclic group. The aliphatic amino acid may be present at one or both ends of the oligomer. Of particular interest are glycine and alanine, for space-shifting, β-alanine is preferred. Usually, a consecutive sequence of 6 heterocycles will be avoided. Generally, there will be an amino acid, particularly β-alanine, introduced in an otherwise consecutive series of six oligomer units, generally bordered by at least two, preferably at least three organic cyclic groups, particularly heterocycles. The following table indicates the effect of extension of the oligomer heterocycles without introducing an amino acid in the chain.

TABLE 1*

| polyamide | sub-unit | binding site size, bp | match | mis-match | specificity⁻ |
|---|---|---|---|---|---|
| Im-(Py)$_2$-Dp | 3 | 5 | 1.3 × 10$^5$ (0.3) | <2 × 10$^{4'}$ | >6.5$^{\&}$ |
| Im-(Py)$_3$-Dp | 4 | 6 | 8.5 × 10$^6$ (1.3) | 1.6 × 10$^6$ (0.2) | 5.3 (0.5) |
| Im-(Py)$_4$-Dp | 5 | 7 | 4.5 × 10$^7$ (1.1) | 7.9 × 10$^6$ (1.8) | 5.7 (0.8) |
| Im-(Py)$_5$-Dp | 6 | 8 | 5.3 × 10$^7$ (0.5) | <2 × 10$^7$ | >2.7$^{\&}$ |
| Im-(Py)$_6$-Dp | 7 | 9 | 4.7 × 10$^7$ (0.4) | 1.7 × 10$^7$ (0.7) | 2.8 (0.7) |
| Im-(Py)$_7$-Dp | 8 | 10 | <2 × 10$^7$ | <2 × 10$^{6'}$ | ⁻1 |

*Values reported are the mean values from at least three footprint titration experiments. Numbers in parentheses indicate the standard deviation for each data set. The assays were performed at 22° C., pH 7.0, in the presence of 10 mM TrisHCl, 10 mM KCl, 10 mM MgCl$_2$ and 5 mM CaCl$_2$.
⁻Defined as the ratio of the match site affintiy to the affinity of the single base pair mismatch site. Numbers in parentheses indicate the uncertainty calculated using the standard deviations of the measured binding affinities.
$^{\&}$Represents a lower limit on the specificity.
'Represents an upper limit for the binding affinity.

The aliphatic chains of the aliphatic amino acids may serve as sites of substitution, the aliphatic amino acid providing a core structure, there usually being not more than 2, more usually not more than 1, substituent. The same types of substituents that have been described for the heterocycles may also be employed here. Conveniently, the substituted aliphatic amino acid may be used in the synthesis of the oligomer, rather than modifying the amino acid after the oligomer is formed. Alternatively, a functional group may be present on the chain of the substituent, if necessary being appropriately protected during the course of the synthesis, which functional group may then be used for the subsequent modification. Desirably, such functional group could be selectively used, for synthesis of different oligomers, so as to provide for substitution at that site to produce products having unique properties associated with a particular application. With the substituent substituted at a site which does not significantly interfere with the binding in the groove, e.g. employing a single stereoisomer, properties can be imparted to the subject compounds, such as water solubility, lipophilicity, non-covalent binding to a receptor, radioactivity, fluorescence, etc.

One or both termini, preferably one of the termini, will have a polar group substituted on an alkyl group, where the polar group will generally be from 2 to 6, more usually 2 to 4, carbon atoms from the linkage to the remaining molecule. The polar group may be charged or uncharged, where the charge may be a result of protonation under the conditions of use. Particularly, groups capable of hydrogen bonding are preferred, such as amino, particularly tertiary-amino, hydroxyl, mercapto, and the like. Of particular interest is amino, more particularly alkylated amino, where the alkyl groups are of from 1 to 6, usually 1 to 3, more usually 1, carbon atom, and at a pH less than about eight, the amino group is positively charged, and can hydrogen bond with the dsDNA. Desirably, two positively charged polar groups will not be employed on the oligomers, where the positively charged polar groups will be in juxtaposition when complexed with the dsDNA. It is found that the presence of the two positively charged polar groups in proximity tends to reduce the binding affinity of the oligomer.

For many purposes one may wish to have an isotopic oligomer, where one can analyze for its presence, using scintillation counters for radioactive elements, nmr for atoms having a magnetic moment, and the like. For a radioactive oligomer, a radioactive label may be employed, such as tritium, $^{14}C$, $^{125}I$, or the like. The radiolabel may be a substituent on an annular member of a heterocycle or an annular member of a heterocycle, either carbon or a heteroatom, or a substituent at the C- or N-terminus of the oligomer, depending upon convenience. By using a radiolabel as part of the oligomer, one avoids any significant change in the spatial conformation of the oligomer. The radiolabel may serve numerous purposes in diagnostics, cytohistology, radiotherapy, and the like.

Besides the other sites present on the oligomer, either terminus of the oligomer may be used for special purposes depending upon the use to which the oligomer is put. For example, in diagnostics, one may wish to have a detectable label other than a radiolabel, where the resulting compound may find use for other purposes, as well. The oligomer may be linked to labels, such as fluorescers, e.g. dansyl, fluorescein, Texas red, isosulfan blue, ethyl red, malachite green, etc., chemiluminescers, particles, e.g. magnetic particles, colloidal particles, e.g. gold particles, light sensitive bond forming compounds, e.g. psoralens, anthranilic acid, pyrene, anthracene, and acridine, chelating compounds, such as EDTA, NTA, tartaric acid, ascorbic acid, polyhistidines of from 2 to 8 histidines, alkylene polyamines, etc., chelating antibiotics, such as bleomycin, where the chelating compounds may chelate a metal atom, such as iron, cobalt, nickel, technetium, etc., where the metal atom may serve to cleave DNA in the presence of a source of peroxide, intercalating dyes, such as ethidium bromide, thiazole orange, thiazole blue, TOTO, 4',6-diamidino-2-phenylindole (DAPI), etc., enzymes, such as β-galactosidase, NADH or NADHP dehydrogenase, malate dehydrogenase, lysozyme, peroxidase, luciferase, etc., alkylating agents such as haloacetamides, N-ethyl nitrosourea, nitrogen and sulfur mustards, sulfonate esters, etc., and other compounds, such as arylboronic acids, tocopherols, lipoic acid, captothesin, etc. colloidal particles, e.g. gold particles, fluorescent particles, peroxides, DNA cleaving agents, oligonucleotides, oligopeptides, nmr agents, stable free radicals, metal atoms, etc. The oligomer may be combined with other labels, such as haptens for which a convenient receptor exists, e.g. biotin, which may be complexed with avidin or streptavidin and digoxin, which may be complexed with antidigoxin, etc. where the receptor may be conjugated with a wide variety of labels, such as those described above. The oligomers may be joined to sulfonated or phosphonated aromatic groups, e.g. naphthalene, to enhance inhibition of transcription, particularly of viruses (Clanton et al., Antiviral Res. (1995) 27:335–354). In some instances, one may bond multiple copies of the subject oligomers to polymers, where the subject oligomers are pendant from the polymer. Polymers, particularly water soluble polymers, which may find use are cellulose, poly(vinyl alcohol), poly(vinyl acetate-vinyl alcohol), polyacrylates, and the like. The number of oligomers may be from 1 to about 1:5 monomer units of the polymer.

One may wish to enhance the lipophilicity of the molecule, providing for various lipophilic groups, such as cholesterol, fatty acids, fatty alcohols, sphingomyelins, cerebrosides, other glycerides, and the like, where the fatty group will generally be of from about eight to thirty carbon atoms. Alternatively, one may wish to provide for saccharides, which bind to lectins, adhesion molecules, bacteria, or the like, where the saccharides serve to direct the subject oligomers to a specific cellular target. Alternatively, in some instances, one may wish to have one or more nucleotides, generally from about one to thirty, more usually from about three to twenty, particularly from about three to twelve. The nucleotides will normally be associated with the proximal or bordering nucleic acid sequence of the target sequence, whereby the attached nucleic acid sequence will complex with the nucleotides in the major groove.

The different molecules may be joined to the termini in a variety of ways, depending upon the available functionality (ies) present at the termini, such as extending the polar substituted alkyl group, e.g. having a chain of more than 6 carbon atoms, providing for a substituent at a terminus which can be reacted with the moiety to be added, where such substituents will conventionally be amino, hydroxyl, mercapto, carboxyl, phosphate, etc., so as to form amides, both organic and inorganic, substituted amines (reductive amination), ethers, thioethers, disulfides, esters, both organic and inorganic, pyrophosphates, and the like. The molecules may be introduced as part of the synthetic scheme, displacing the oligomer from the solid support on which the oligomer is synthesized. Because the compounds of the subject invention may be used in such a variety of ways, no simple description is appropriate to the variety of moieties to which the subject oligomers may be bound, nor the specific molecular weights of the resulting products.

The subject oligomers may be synthesized on supports, e.g. chips, where by using automated synthetic techniques, different oligomers may be synthesized at individual sites. In this way, an array of different oligomers may be synthesized, which can then be used to identify the presence of a plurality of different sequences in a sample. By knowing the composition of the oligomer at each site, one can identify binding of specific sequences at that site by various techniques, such as labeled antiDNA antibodies, linkers having complementary restriction overhangs, where the sample DNA has been digested with a restriction enzyme, and the like. The techniques for preparing the subject arrays are analogous to the techniques used for preparing oligopeptide arrays, as described in Cho et al., Science, 1993, 261, 1303–1305.

The complex will usually comprise one or two oligomers or combinations of one or two oligomers, where individual or pairs of oligomers specifically interact with a dsDNA sequence of at least 6, usually at least 7 and preferably 8 or more bp, frequently not more than 40 bp, more usually not more than about 30 bp, preferably not more than 20 bp.

Since a major portion of the work has been performed with N-methyl pyrrole and N-methyl imidazole, using carbamyl groups as the linking chains, with the aliphatic amino acids glycine, β-alanine and γ-aminobutyric acid, as well as dimethylaminopropyl as the polar substituted alkyl group, these compounds will now be illustrated as exemplary of the class of compounds which may be employed in the subject invention. It is understood that one or a few of the nitrogen-heterocycles may be substituted with a different organic cyclic group, as well one or the other of the aliphatic amino acids may be substituted with a different amino acid, etc. Furthermore, the core oligomer may be further substituted for specific applications as described above. In effect, there is a core molecule or core molecules which define at least complementary pairs of heterocycles, and include at least one of an aliphatic amino acid and a polar group substituted alkyl. This core molecule which is the centerpiece of the invention can serve as the nexus for numerous substitutions which do not interfere with the basic function of the core molecule, although where the binding affinity is greater than is necessary for the function, some degradation of the binding affinity is permitted. Therefore, in defining the compounds of this invention, it should be understood that many variations are permitted, where the basic core or unit structure is retained, while the core or unit structure is modified with one or more substituents to impart desired properties to the molecule for its intended function.

Of particular interest among the subject compounds are compounds which have at least one organic cyclic group, particularly N-methyl imidazole, which has specificity for one nucleotide, which is present as a complementary pair. Usually, the subject compounds will have at least one of these complementary pairs, frequently at least two of these complementary pairs, and generally fewer than 75% of the complementary pairs will have the organic cyclic group having specificity for a single nucleotide. In the case of the N-methyl imidazole, there will usually be at least one Im/Py pair, desirably not having more than three, frequently having not more than two, of such pairs consecutively, so that there will frequently be not more than three Im's in a row. There will normally be at least one aliphatic amino acid, frequently two aliphatic amino acids, and frequently not more than eight aliphatic amino acids, usually not more than six aliphatic amino acids, more usually not more than about four aliphatic amino acids. Preferably, there will be an amino acid proximal to at least one terminus of the oligomer. The Im/Py pair provide for greater specificity, but contribute less than the Py/Py pair to the binding affinity for the dsDNA. Therefore, by appropriate selection of the target sequence, one may optimize for binding affinity and specificity.

It is found that with β-alanine, β-alanine associates with T-A pairs and will usually form a complementary pair with itself. Thus, β-alanine may be used in juxtaposition to T or A and as a complementary pair with itself with a T-A pair.

The binding affinity $K_s$ as determined in the Experimental section will be greater than $5 \times 10^8$ $M^{-1}$, usually greater than $10^9$ $M^{-1}$, preferably greater than about $10^{10}$ $M^{-1}$, so as to be able to bind to the target sequence at subnanomolar concentrations in the environment in which they are used. The difference in affinity with a single mismatch will be at least 3 fold, usually at least 5 fold, preferably at least 10 fold and frequently greater than 20 fold, and may be 100 fold or more.

Where the oligomers of the subject invention are used with cells, particularly viable cells, the oligomers will generally have a molecular weight of less than about 5 kD, preferably less than about 3.5 kD, and will generally have a molecular weight of at least about 0.6 kD, more usually at least about 0.8 kD.

The compositions of the subject invention for complexing with dsDNA will have from one to two oligomers, or combinations thereof, depending upon whether there is a hairpin turn in the oligomer, where only one oligomer is necessary, or there is no hairpin turn, so that for complementarity, one needs two oligomers. More oligomers may be used, where one wishes to target more than one dsDNA sequence, for example, contiguous or proximal sequences, to enhance the overall specificity, or for distal sequences, where the sequences may be associated with the same functional unit, e.g. a gene, or different functional units, e.g. homeodomains. The composition, whether a single oligomer or a combination of oligomers will provide at least three complementary pairs in the single oligomer or pair of oligomers.

In many cases, in order to achieve the desired association constants, one will increase the number of complementary pairs and/or have regions of unpaired organic cyclic groups. Usually, one will have at least one or both of a fourth complementary pair or three unpaired organic cyclic groups, so as to have a chain of four organic cyclic groups involved in pair formation and/or three organic cyclic groups uninvolved with pair formation. It is found that one does not increase the binding affinity to the same extent with each addition of an organic cyclic unit, as one extends the length of the oligomer and, in fact, as described previously, one may begin to reverse the binding affinity by the continuous extension. Therefore, by appropriate choice, as indicated above, one can limit the composition and size of individual oligomers to optimize the binding affinity, as well as the other properties which are associated with the oligomeric composition.

Because of the extensive utilization of N-methyl pyrrole and N-methyl imidazole, the following compounds which employ these N-heterocycles are exemplary of the class of compounds of the subject invention. These compounds may be prepared in accordance with the procedures described herein. When used, Py will refer to N-methyl pyrrole and Im will refer to N-methyl imidazole.

ImPyPyPy-γ-PyPyPyPy, PyPyImPy-γ-PyPyPyPy, ImPyPyPy-γ-ImPyPyPy, PyImPyPy-γ-PyImPyPy, ImPyImPy-γ-PyPyPyPy, ImImPyPy-γ-PyPyPyPy, ImImImPy-γ-PyPyPyPy, ImImPyPy-γ-ImPyPyPy, ImPyPyPy-γ-PyPyPyPy, ImImPyPy-γ-ImImPyPy, ImPyPyPy-γ-ImImPyPy, ImImPyPy-γ-ImImPyPy, ImPyImPy-γ-ImPyImPy, ImImImPy-γ-ImPyPyPy, ImImImIm-γ-PyPyPyPy, Im-β-PyPy-γ-Im-β-PyPy, Im-β-ImIm-γ-Py-β-PyPy, Im-β-ImPy-γ-Im-β-ImPy, ImPyPyPyPy-γ-ImPyPyPyPy, ImImPyPyPy-γ-ImPyPyPyPy, ImPyImPyPy-γ-ImPyPyPyPy, ImImPyImIm-γ-PyPyPyPyPy, ImPyPyImPy-γ-ImPyPyImPy, ImPy-β-PyPy-γ-ImPy-β-PyPy, ImIm-β-ImIm-γ-PyPy-β-PyPy, ImPy-β-ImPy-γ-ImPy-β-ImβPy ImPy-β-PyPyPy-γ-ImPyPy-β-PyPy, ImIm-β-PyPyPy-γ-PyPyPy-β-PyPy, ImPy-β-ImPyPy-γ-ImPyPy-β-PyPy, ImIm-β-PyPyPy-γ-ImImPy-β-PyPy, ImPy-β-PyPyPy-γ-PyPyPy-β-ImPy, ImPyPyPyPyPy-γ-ImPyPyPyPyPy, ImPyPy-β-PyPy-γ-ImPyPy-β-PyPy, ImPyPyPy-β-Py-γ-Im-β-PyPyPyPy, ImImPyPyPyPy-γ-ImImPyPyPyPy, Im-β-PyPyPyPy-γ-Im-β-PyPyPyPy, ImPyPyPy-β-Py-γ-ImPyPyPy-β-Py, ImPyImPyPyPy-γ-ImPyPyPyPyPy, ImPyPy-β-PyPy-γ-ImPy-β-PyPyPy, ImPyPyPyPy-β-γ-ImPyPyPyPy-β, ImPy-β-ImPyPy-γ-ImPy-β-ImPyPy, Im-β-PyPyPyPy-γ-ImPyPyPy-β-Py, Im-β-ImPyPyPy-γ-ImPyPyPy-β-Py, ImPyPy-β-PyPyPy, ImImPy-β-PyPyPy, ImImIm-β-PyPyPy, ImPyPyPyPy-β-PyPyPy, ImPyPyPy-β-PyPyPy, ImPyPy-β-PyPyPyPyPy, ImPyPyPy-β-PyPyPyPy, ImImPyPy-β-PyPyPyPy, ImImImPy-β-PyPyPyPy, ImPyPyPy-β-ImPyPyPy, ImImPyPy-β-ImPyPyPy, ImImPyPy-β-ImPyPyPy, ImImPyPyPy-β-PyPyPyPyPy, ImImImPyPy-β-PyPyPyPy, ImIm-β-PyPy-β-PyPy-β-PyPy, ImImPy-β-PyPyPy-β-PyPyPy, ImImPyPy-β-Py-β-PyPyPy, ImPyPy-γ-ImPyPy-β-PyPyPy, ImPyPy-γ-PyPyPy-β-PyPyPy, PyImPy-γ-ImPyPy-β-PyPyPy, PyImPy-γ-ImPyPy-β-PyPyPy, PyImPy-γ-ImPyPy-β-PyPyPy-β-PyPyPy, ImImPy-γ-ImPyPy-β-PyPyPy, ImPyPy-γ-ImPyPy-G-PyPyPy, ImPyPyPy-γ-ImImImPy-β-PyPyPyPy, ImImPyPyPy-γ-ImImPyPy-β-PyPyPyPy, and ImImPyPyPy-γ-PyPyPyPy-β-PyPyPy, PyPyImIm, ImPy-β-ImPy-β-ImPy, ImPy-β-ImPy-β-ImPy-β-PyPy, ImPy-β-ImPy-β-ImPy-γ-ImPy-β-ImPy-β-ImPy, ImPy-β-PyPy-β-PyPy, ImPy-β-PyPy-β-PyPy-γ-ImPy-β-PyPy-β-PyPy, Im-β-ImImImIm-γ-PyPyPyPy-β-Py, Im-β-

ImImImIm-β-Im-γ-Py-β-PyPyPyPy-β-Py,
ImIm-β-Im-γ-Py-β-PyPyPyPy-β-Py, Im-β-ImPyPy-γ-
ImImPy-β-Py, ImImPy-β-Py-γ-Im-β-ImPyPy,
ImIm-β-Im-γ-PyImPyPy.

FIG. 1 illustrates the relationship between the azoles and the nucleotides of the minor groove.

Where two oligomers are used, the oligomers may be completely overlapped, or only partially overlapped, i.e. slipped or have overhangs. As indicated previously, there will be at least 3 complementary azole (N-methyl pyrrole and imidazole)pairs. In the overlapped configuration, all of the azoles are in complementary pairs, as well as any spacing amino acid. In the slipped configuration, there will be at least one azole ring which is unpaired in at least one of the oligomers, usually there will be at least two azole rings, more usually, in both of the oligomers. Usually, the number of unpaired azole rings will be in the range of 2 to 30, more usually 2 to 20, frequently 2 to 12. Generally, unpaired azoles will involve chains of 2 or more azole rings, more usually 3 or more azole rings, including, as appropriate, aliphatic amino acids in the chain.

Various permutations and combinations of oligomers may be used. One may have a single oligomer having at least three complementary pairs and an extension or overhang of unpaired azoles, which may be complemented in whole or part by a second oligomer, which forms complementary pairs with the unpaired members of the first oligomer. Alternatively, one may have two "candy cane" oligomers, having complementary pairs, with the members of the complementary pairs separated by a γ-aminobutyric acid, and an overhang of unpaired members. However, these otherwise unpaired members of one oligomer can be positioned to form complementary pairs with the extension or overhang of the unpaired members of the other oligomer. One may have an extended linear oligomer, where two or more oligomers complement the azoles of the extended linear oligomer. If one wished, one could have alternating regions of unpaired and paired azoles by using a plurality of oligomers which complement to various degrees. In each case, the selection would be related to the desired affinity, the nature of the target, the purpose for the formation of the complex, and the like.

The subject compositions may be brought together with the dsDNA under a variety of conditions. The conditions may be in vitro, in cell cultures, ex vivo or in vivo. For detecting the presence of a target sequence, the dsDNA may be extracellular or intracellular. When extracellular, the dsDNA may be in solution, in a gel, on a slide, or the like. The dsDNA may be present as part of a whole chromosome or fragment thereof of one or more centiMorgans. The dsDNA may be part of an episomal element. The dsDNA may be present as smaller fragments ranging from about 20, usually at least about 50, to a million base pairs, or more. The dsDNA may be intracellular, chromosomal, mitochondrial, plastid, kinetoplastid, or the like, part of a lysate, a chromosomal spread, fractionated in gel elecrophoresis, a plasmid, or the like, being an intact or fragmented moiety. The formation of complexes between dsDNA and the subject compounds may be for diagnostic, therapeutic, purification, or research purposes, and the like. Because of the specificity of the subject compounds, the subject compounds can be used to detect specific dsDNA sequences in a sample without melting of the dsDNA. The diagnostic purpose for the complex formation may be detection of alleles, identification of mutations, identification of a particular host, e.g. bacterial strain or virus, identification of the presence of a particular DNA rearrangement, identification of the presence of a particular gene, e.g. multiple resistance gene, forensic medicine, or the like. With pathogens, the pathogens may be viruses, bacteria, fungi, protista, chlamydia, or the like. With higher hosts, the hosts may be vertebrates or invertebrates, including insects, fish, birds, mammals, and the like or members of the plant kingdom.

When involved in vitro or ex vivo, the dsDNA may be combined with the subject compositions in appropriately buffered medium, generally at a concentration in the range of about 0.1 nM to 1 mM. Various buffers may be employed, such as TRIS, HEPES, phosphate, carbonate, or the like, the particular buffer not being critical to this invention. Generally, conventional concentrations of buffer will be employed, usually in the range of about 10–200 mM. Other additives which may be present in conventional amounts include sodium chloride, generally from about 1–250 mM, dithiothreitol, and the like. The pH will generally be in the range of about 6.5 to 9. The target dsDNA may be present in from about 0.001 to 100 times the moles of oligomer.

The subject compounds when used in diagnosis may have a variety of labels as indicated previously and may use many of the protocols that have been used for detection of haptens and receptors (immunoassays) or with hybridization (DNA complementation). Since the subject compounds are not nucleic acids, they can be employed more flexibly than when using DNA complementation. The assays are carried out as described below and then depending on the nature of the label and protocol, the determination of the presence and amount of the sequence may then be made. The protocols may be performed in solution or in association with a solid phase. The solid phase may be a vessel wall, a particle, fiber, film, sheet, or the like, where the solid phase may be comprised of a wide variety of materials, including gels, paper, glass, plastic, metals, ceramics, etc. Either the sample or the subject compounds may be affixed to the solid phase in accordance with known techniques. By appropriate functionalization of the subject compounds and the solid phase, the subject compounds may be covalently bound to the solid phase. The sample may be covalently or non-covalently bound to the solid phase, in accordance with the nature of the solid phase. The solid phase allows for a separation step, which allows for detection of the signal from the label in the absence of unbound label.

Exemplary protocols include combining a cellular lysate, with the DNA bound to the surface of a solid phase, with an enzyme labeled oligomer, incubating for sufficient time under complex forming conditions for the oligomer to bind to any target sequence present on the solid phase, separating the liquid medium and washing, and then detecting the presence of the enzyme on the solid phase by use of a detectable substrate.

A number of protocols are based on having a label which does not give a detectable signal directly, but relies on non-covalent binding with a receptor, which is bound to a surface or labeled with a directly detectable label. In one assay one could have a hapten, e.g. digoxin, bonded to the oligomer. The sample DNA would be bound to a surface, so as to remain bound to the surface during the assay process. The oligomer would be added and bind to any target sequence present. After washing to remove oligomer, enzyme or fluorescer labeled antidigoxin monclonal antibody is added, the surface washed and the label detected. Alternatively, one may have a fluorescer bound to one end of the oligomer and biotin or other appropriate hapten bound to the other end of the oligomer or to the complementary oligomer. The oligomers are combined with the DNA in the liquid phase and incubated. After completion of the incubation, the sample is combined with the receptor for the biotin or hapten, e.g. avidin or antibody, bound to a solid surface. After a second incubation, the surface is washed and the level of fluorescence determined.

If one wishes to avoid a separation step, one may use channeling or fluorescence quenching. By having two labels which interact, for example, two enzymes, where the product of one enzyme is the substrate of the other enzyme, or two fluorescers, where there can be energy transfer between the two fluorescers, one can determine when complex formation occurs, since the two labels will be brought into juxtaposition by forming the 2:1 complex in the minor groove. With the two enzymes, one detects the product of the second enzyme and with the two fluorescers, one can determine fluorescence at the wavelength of the Stokes shift or reduction in fluorescence of the fluorescer absorbing light at the lower wavelength. Another protocol would provide for binding the subject compositions to a solid phase and combining the bound oligomers with DNA in solution. After the necessary incubations and washings, one could add labeled antiDNA to the solid phase and determine the amount of label bound to the solid phase.

To determine a number of different sequences simultaneously or just a single sequence, one may provide an array of the subject compositions bound to a surface. In this way specific sites in the array will be associated with specific DNA sequences. One adds the DNA containing sample to the array and incubates. DNA which contains the complementary sequence to the oligomer at a particular site will bind to the oligomers at that site. After washing, one then detects the presence of DNA at particular sites, e.g. with an antiDNA antibody, indicating the presence of the target sequence. By cleaving the DNA with a restriction enzyme in the presence of a large amount of labeled linker, followed by inactivation of the enzyme, one may then ligate the linker to the termini of the DNA fragments and proceed as described above. The presence of the label at a particular site in the array will indicate the presence of the target sequence for that site.

The number of protocols that may be used is legion. Illustrative protocols may be found for DNA assays in WO95/20591; EPA 393,743; WO86/05519; and EPA 278,220, while protocols and labels which may be adapted from immunoassays for use with the subject compositions for assays for DNA may be found in WO96/20218; WO95/06115; WO94/04538; WO94/01776; WO92/14490; EPA 537830; WO91/09141; WO91/06857; and WO91/05257.

During diagnostics, such as involved with cells, one may need to remove the non-specifically bound oligomers. This can be achieved by combining the cells with a substantial excess of the target sequence, conveniently attached to particles. By allowing for the non-specifically bound oligomers to move to the extracellular medium, the oligomers will become bound to the particles, which may then be readily removed. If desired, one may take samples of cells over time and plot the rate of change of loss of the label with time. Once the amount of label becomes stabilized, one can relate this value to the presence of the target sequence. Other techniques may also be used to reduce false positive results.

The subject compositions may also be used to titrate repeats, where there is a substantial change, increase or decrease, in the number of repeats associated with a particular indication. The number of repeats should be at least an increase of 50%, preferably at least two-fold, more preferably at least three-fold. By determining the number of oligomers which become bound to the dsDNA, one can determine the amplification or loss of a particular repeat sequence.

The subject compositions may be used for isolation and/or purification of target DNA comprising the target sequence. By using the subject oligomers, where the oligomers are bound to a solid phase, those portions of a DNA sample which have the target sequence will be bound to the subject oligomers and be separated from the remaining DNA. One can prepare columns of particles to which the oligomers are attached and pass the sample through the column. After wishing the column, one can release the DNA which is specifically bound to the column using solvents or high salt solutions. Alternatively, one can mix particles to which the oligomers are bound with the sample and then separate the particles, for example, with magnetic particles, using a magnetic field, with non-magnetic particles, using centrifugation. In this way, one can rapidly isolate a target DNA sequence of interest, for example, a gene comprising an expressed sequence tag (EST), a transcription regulatory sequence to which a transcription factor binds, a gene for which a fragment is known, and the like. As partial sequences are defined by a variety of techniques, the subject oligomers allow for isolation of restriction fragments, which can be separated on a gel and then sequenced. In this way the gene may be rapidly isolated and its sequence determined. As will be discussed below, the subject oligomers may then be used to define the function of the gene.

The subject oligomers may be used in a variety of ways in research. Since the subject oligomers can be used to inhibit transcription, the effect of inhibiting transcription on cells, cell assemblies and whole organisms may be investigated. For example, the subject compositions may be used in conjunction with egg cells, fertilized egg cells or blastocysts, to inhibit transcription and expression of particular genes associated with development of the fetus, so that one can identify the effect of reduction in expression of the particular gene. Where the gene may be involved in regulation of a number of other genes, one can define the effect of the absence of such gene on various aspects of the development of the fetus. The subject oligomers can be designed to bind to homeodomains, so that the transcription of one or more genes may be inhibited. In addition, one can use the subject compositions during various periods during the development of the fetus to identify whether the gene is being expressed and what the effect is of the gene at the particular stage of development.

With single cell organisms, one can determine the effect of the lack of a particular expression product on the virulence of the organism, the development of the organism, the proliferation of the organism, and the like. In this way, one can determine targets for drugs to inhibit the growth and infectiousness of the organism.

In an animal model, one can provide for inhibition of expression of particular genes, reversibly or irreversibly, by administering the subject compositions to the host in a variety of ways, oral or parenteral, by injection, at a particular site where one wishes to influence the transcription, intravascularly, subcutaneously, or the like. By inhibiting transcription, one can provide for a reversible "knock out," where by providing for continuous intravenous administration, one can greatly extend the period in which the transcription of the gene is inhibited. Alternatively, one may use a bolus of the subject oligomers and watch the effect on various physiological parameters as the bolus becomes dissipated. One can monitor the decay of the effect of the inhibition, gaining insight into the length of time the effect lasts, the physiological processes involved with the inhibition and the rate at which the normal physiological response occurs. Instead, one can provide for covalent bonding of the oligomer to the target site, using alkylating agents, light activated bonding groups, intercalating groups, etc.

It is also possible to upregulate genes, by downregulating other genes. In those instances where one expression product inhibits the expression of another expression product, by inhibiting the expression of the first product, one can enhance the expression of the second product. Similarly, transcription factors involve a variety of cofactors to form a complex, one can enhance complex formation with one transcription factor, as against another transcription factor, by inhibiting expression of the other transcription factor. In this way one can change the nature of the proteins being expressed, by changing the regulatory environment in the cell.

The target sequence may be associated with the 5'-untranslated region, namely the transcriptional initiation region, an enhancer, which may be in the 5'-untranslated region, the coding sequence or introns, the coding region, including introns and exons, the 3'-untranslated region, or distal from the gene.

The subject compositions may be presented as liposomes, being present of the lumen of the liposome, where the liposome may be combined with antibodies to surface membrane proteins or basement membrane proteins, ligands for cellular receptors, or other site directing compound, to localize the subject compositions to a particular target. See. for example, Theresa and Mouse, Adv. Drug Delivery Rev. 1993, 21, 117–133; Huwyler and Partridge, Proc. Natl. Acad. Sci. USA 1996, 93, 11421–11425; Dzau et al., Proc. Natl. Acad. Sci. USA 1996, 93, 11421–11425; and Zhu et al., Science, 1993, 261, 209–211. The subject compositions may be administered by catheter to localize the subject compositions to a particular organ or target site in the host. Generally, the concentration at the site of interest should be at least about 0.1 nM, e.g. intracellular or in the extracellular medium, preferably at least about 1 nM, usually not exceeding 1mM, more usually not exceeding about 100 nM. To achieve the desired intracellular concentration, the concentration of the oligomers extracellularly will generally be greater than the desired intracellular concentration, ranging from about 2 to 1000 times or greater the desired intracellular concentration. Of course, where the toxicity profile allows for higher concentrations than those indicated for intracellular or extracellular concentrations, the higher concentrations may be employed, and similarly, where the affinities are high enough, and the effect can be achieved with lower concentrations, the lower concentrations may also be employed.

The subject compositions can be used to modulate physiological processes in vivo for a variety of reasons. In non-primates, particularly domestic animals, in animal husbandry and breeding, one can affect the development of the animal by controlling the expression of particular genes, modify physiological processes, such as accumulation of fat, growth, response to stimuli, etc. One can also use the subject compositions for therapeutic purposes in mammals. Domestic animals include feline, murine, canine, lagomorpha, bovine, ovine, canine, porcine, etc.

The subject compositions may used therapeutically to inhibit proliferation of particular target cells, inhibit the expression of one or more genes related to an indication, change the phenotype of cells, either endogenous or exogenous to the host, where the native phenotype is detrimental to the host. Thus, by providing for binding to housekeeping or other genes of bacteria or other pathogen, particularly genes specific to the pathogen, one can provide for inhibition of proliferation of the particular pathogen. Various techniques may be used to enhance transport across the bacterial wall, such as various carriers or sequences, such as polylysine, poly(E-K), nuclear localization signal, cholesterol and cholesterol derivatives, liposomes, protamine, lipid anchored polyethylene glycol, phosphatides, such as dioleoxyphosphatidylethanolamine, phosphatidyl choline, phosphatidylglycerol, α-tocopherol, cyclosporin, etc. In many cases, the subject compositions may be mixed with the carrier to form a dispersed composition and used as the dispersed composition. Similarly, where a gene may be essential to proliferation or protect a cell from apoptosis, where such cell has undesired proliferation, the subject compositions can be used to inhibit the proliferation by inhibiting transcription of essential genes. This may find application in situations such as cancers, such as sarcomas, carcinomas and leukemias, restenosis, psoriasis, lymphopoiesis, atherosclerosis, pulmonary fibrosis, primary pulmonary hypertension, neurofibromatosis, acoustic neuroma, tuberous sclerosis, keloid, fibrocystic breast, polycystic ovary and kidney, scleroderma, rheumatoid arthritis, ankylosing spondilitis, myelodysplasia, cirrhosis, esophageal stricture, sclerosing cholangitis, retroperitoneal fibrosis, etc. Inhibition may be associated with one or more specific growth factors, such as the families of platelet-derived growth factors, epidermal growth factors, transforming growth factor, nerve growth factor, fibroblast growth factors, e.g. basic and acidic, keratinocyte fibroblast growth factor, tumor necrosis factors, interleukins, particularly interleukin 1, interferons, etc. In other situations, one may wish to inhibit a specific gene which is associated with a disease state, such as mutant receptors associated with cancer, inhibition of the arachidonic cascade, inhibition of expression of various oncogenes, including transcription factors, such as ras, myb, myc, sis, src, yes, fps/fes, erbA, erbB, ski, jun, crk, sea, rel, fms, abl, met, trk, mos, Rb-1, etc. Other conditions of interest for treatment with the subject compositions include inflammatory responses, skin graft rejection, allergic response, psychosis, sleep regulation, immune response, mucosal ulceration, withdrawal symptoms associated with termination of substance use, pathogenesis of liver injury, cardiovascular processes, neuronal processes,Particularly, where specific T-cell receptors are associated with autoimmune diseases, such as multiple sclerosis, diabetes, lupus erythematosus, myasthenia gravis, Hashimoto's disease, cytopenia, rheumatoid arthritis, etc., the expression of the undesired T-cell receptors may be diminished, so as to inhibit the activity of the T-cells. In cases of reperfusion injury or other inflammatory insult, one may provide for inhibition of enzymes associated with the production of various factors associated with the inflammatory state and/or septic shock, such as TNF, enzymes which produce singlet oxygen, such as peroxidases and superoxide dismutase, proteases, such as elastase, INFγ, IL-2, factors which induce proliferation of mast cells, eosinophils, $IgG_1$, IgE, regulatory T cells, etc., or modulate expression of adhesion molecules in leukocytes and endothelial cells.

Other opportunities for use of the subject compositions include modulating levels of receptors, production of ligands, production of enzymes, production of factors, reducing specific cell populations, changing phenotype and genotype of cells, particularly as associated with particular organs and tissues, modifying the response of cells to drugs or other stimuli, e.g. enhancing or diminishing the response, inhibiting one of two or more alleles, repressing expression of target genes, particularly as related to clinical studies, modification of behavior, modification of susceptibility to disease, response to stimuli, response to pathogens, response to drugs, therapeutic or substances of abuse, etc.

Individual compositions may be employed or combinations, directed to the same dsDNA region, but different target sequences, contiguous or distal, or different DNA regions. Depending upon the number of genes which one wishes to target, the composition may have one or a plurality of oligomers or pairs of oligomers which will be directed to different target sites.

The subject compositions may be used as a sole therapeutic agent or in combination with other therapeutic agents. Depending upon the particular indication, other drugs may also be used, such as antibiotics, antisera, monoclonal antibodies, cytokines, anti-inflammatory drugs, and the like. The subject compositions may be used for acute situations or in chronic situations, where a particular regimen is devised for the treatment of the patient. The compositions may be prepared in physiologically acceptable media and stored under conditions appropriate for their stability. They may be prepared as powders, solutions or dispersions, in aqueous media, alkanols, e.g. ethanol and propylene glycol, in conjunction with various excipients, etc. The particular formulation will depend upon the manner of administration, the desired concentration, ease of administration, storage stability, and the like. The concentration in the formulation will depend upon the number of doses to be administered, the activity of the oligomers, the concentration required as a therapeutic dosage, and the like. The subject compositions may be administered orally, parenterally, e.g. intravenously, subcutaneously, intraperitoneally, transdermally, etc. The subject compositions may be formulated in accordance with conventional ways, associated with the mode of treatment. As a result of the formulation, the subject compositions are introduced into the cells, either as a directed introduction to a specific cell target or as random introduction into a number of different cell types. However, the subject compositions will only have an effect in those cells in which the target dsDNA is being transcribed or there is some other mechanism whereby the binding of the subject compositions can affect the mechanism. In this way selectivity can be achieved, since the only productive result will be in cells where the target dsDNA has an effect which is modified by the binding of the subject compositions to the dsDNA.

The subject compounds may be prepared, conveniently employing a solid support. See, for example, Baird and Dervan, J. Am. Chem. Soc. 1996, 118, 6141; PCT application, US97/03332. For solid phase synthesis, the oligomer is grown on the solid phase attached to the solid phase by a linkage which can be cleaved by a single step process. The addition of an aliphatic amino acid at the C-terminus of the oligomers allows the use of Boc-β-alanine-Pam-resin which is commercially available in appropriate substitution levels (0.2 mmol/g). Aminolysis may be used for cleaving the polyamide from the support. In the case of the N-methyl 4-amino-2-carboxypyrrole and the N-methyl 4-amino-2-carboxyimidazole, the tert.-butyl esters may be employed, with the amino groups protected by Boc or Fmoc, with the monomers added sequentially in accordance with conventional techniques. For further details, see the references cited in the related literature, which are incorporated herein by reference, as well as the Experimental section.

The following examples are offered by way of illustration, and not by way of limitation.

EXPERIMENTAL

EXAMPLE 1

Solid phase synthesis of polyamides containing imidazole and pyrrole amino acids[1]

[1]Baird & Dervan, J. Am. Chem. Soc., 1996, 118, 6141.

Boc-β-alanine-(4-carboxamidomethyl)-benzyl-ester-co-poly(styrene-divinylbenzene) resin (Boc-β-alanine-Pam-Resin), dicyclohexylcarbodiimide (DCC), hydroxybenzotriazole (HOBt), 2-(1H-benzotriazole-1-yl)-1,1,3,3-tetramethyluronium hexafluorophosphate (HBTU), Boc-glycine, and Boc-β-alanine were purchased from Peptides International. N,N-diisopropylethylamine (DIEA), N,N-dimethylformamide (DMF), N-methylpyrrolidone (NMP), and DMSO/NMP were purchased from Applied Biosystems. Boc-γ-aminobutyric acid was from NOVA Biochem, dichloromethane (DCM) and triethylamine (TEA) was reagent grade from EM, thiophenol (PhSH), dimethylaminopropylamine, trichloroacetyl chloride, N-methylpyrrole, and N-methylimidazole from Aldrich, and trifluoroacetic acid (TFA) from Halocarbon. All reagents were used without further purification.

Monomer Syntheses
4-Nitro-2-trichloroacetyl-1-methylpyrrole

To a well stirred solution of trichloroacetyl chloride (1 kg, 5.5 mole) in 1.5 liter ethyl ether in a 12 liter flask was added dropwise over a period of 3 h a solution of N-methylpyrrole (0.45 kg, 5.5 mole) in 1.5 liter anhydrous ethyl ether. The reaction was stirred for an additional 3 hours and quenched by the dropwise addition of a solution of 400 g potassium carbonate in 1.5 liters water. The layers were separated and the ether layer concentrated in vacuo to provide 2-(trichloroacetyl)pyrrole (1.2 kg, 5.1 mol) as a yellow crystalline solid sufficiently pure to be used without further purification. To a cooled (−40° C.) solution of 2-(trichloroacetyl) pyrrole (1.2 kg, 5.1 mol) in acetic anhydride (6 L) in a 12 L flask equipped with a mechanical stirrer was added 440 mL fuming nitric acid over a period of 1 hour while maintaining a temperature of (−40° C.). The reaction was carefully allowed to warm to room temperature and stir an additional 4 h. The mixture was cooled to −30° C., and isopropyl alcohol (6 L) added. The solution was stirred at −20° C. for 30 min during which time a white precipitate forms. The solution was allowed to stand for 15 min and the resulting precipitate collected by vacuum filtration.

Methyl 4-nitropyrrole-2-carboxylate

To a solution of 4-Nitro-2-trichloroacetyl1-methylpyrrole (800 g, 2.9 mol) in 2.5 L methanol in a 4 L Erlenmeyer flask equipped with a mechanical stirrer was added dropwise a solution of NaH (60% dispersion in oil) (10 g, 0.25 mol) in 500 mL methanol. The reaction was stirred 2 h at room temperature, and quenched by the addition of conc. sulfuric acid (25 mL). The reaction was then heated to reflux, allowed to slowly cool to room temperature. Product crystallized as white needles which were collected by vacuum filtration.

Methyl 4-amino-1-methyl-pyrrole-2-carboxylate hydrochloride

Methyl-4-nitropyrrole-2-carboxylate 4 (450 g, 2.8 mol) was dissolved in ethyl acetate (8 L). A slurry of 40 g of 10% Pd/C in 800 mL ethyl acetate was then added and the mixture stirred under a slight positive pressure of hydrogen (c.a. 1.1 atm) for 48 h. Pd/C was removed by filtration through celite, washed 1×50 mL ethyl acetate, and the volume of the mixture reduced to c.a. 500 mL. 7 L of cold ethyl ether was added and HCl gas gently bubbled through the mixture. The precipitated amine hydrochloride was then collected by vacuum filtration to yield a white powder (380 g, 81.6%).

4-[(tert-Butoxycarbonyl)amino]-1-methylpyrrole-2-carboxylic acid

Methyl 4-amino-1-methyl-pyrrole-2carboxylate hydrochloride (340 g, 1.8 mol) was dissolved in 1 L of 10% aqueous sodium carbonate in a 3 L flask equipped with a mechanical stirrer, di-t-butyldicarbonate (400 g, 2.0 mmol) slurried in 500 mL of dioxane was added over a period of thirty min., maintaining a temperature of 20° C. The reaction was allowed to proceed for three h and was determined complete by TLC, cooled to 5° C. for 2 h and the resulting white precipitate collected by vacuum filtration. The Boc-pyrrole ester contaminated with Boc-anhydride was dissolved in 700 mL MeOH, 700 mL of 2M NaOH was added and the solution heated at 60° C. for 6 h. The reaction was cooled to room temperature, washed with ethyl ether (4×1000 mL), the pH of the aqueous layer reduced to c.a. 3 with 10% (v/v) $H_2SO_4$, and extracted with ethyl acetate (4×2000 mL). The combined ethyl acetate extracts were dried (sodium sulfate) and concentrated in vacuo to provide a tan foam. The foam was dissolved in 500 mL of DCM and 2 L petroleum ether added, the resulting slurry was concentrated in vacuo. The reaction was redissolved and concentrated three additional times to provide a fine white powder (320 g, 78% yield).

1,2,3-Benzotriazol-1-yl 4-[(tert-butoxycarbonyl)-amino]-1-methylpyrrole-2-carboxylate Boc-Py-acid (31 g, 129 mmol) was dissolved in 500 mL DMF, HOBt (17.4 g, 129 mmol) was added followed by DCC (34 g, 129 mmol). The reaction was stirred for 24 h and then filtered dropwise into a well stirred solution of 5 L of ice water. The precipitate was allowed to sit for 15 min at 0° C. and then collected by filtration. The wet cake was dissolved in 500 mL DCM, and the organic layer added slowly to a stirred solution of cold petroleum ether (4° C.). The mixture was allowed to stand at −20° C. for 4 h and then collected by vacuum filtration and dried in vacuo to provide a finely divided white powder (39 g, 85% yield).

Ethyl 1-methylimidazole-2-carboxylate

N-methylimidazole (320 g, 3.9 mol) was combined with 2 L acetonitrile and 1 L triethylamine in a 12 L flask equipped with a mechanical stirrer and the solution cooled to −20° C. Ethyl chloroformate (1000 g, 9.2 mol) was added with stirring, keeping the temperature between −20° C. and −25° C. The reaction was allowed to slowly warm to room temperature and stir for 36 h. Precipitated triethylamine hydrochloride was removed by filtration and the solution concentrated in vacuo at 65° C. The resulting oil was purified by distillation under reduced pressure (2 torr, 102° C.) to provide a white solid (360 g, 82% yield).

Ethyl 1-methyl-4-nitroimidazole-2-carboxylate

Ethyl 1-methylimidazole-2-carboxylate was carefully dissolved in 1000 mL of concentrated sulfuric acid cooled to 0° C. 90% nitric acid (1 L) was slowly added maintaining a temperature of 0° C. The reaction was then refluxed with an efficient condenser (−20° C.) in a well ventilated hood for 50 min. The reaction was cooled with an ice bath, and quenched by pouring onto 10 L ice. The resulting blue solution was then extracted with 20 L DCM, the combined extracts dried (sodium sulfate) and concentrated in vacuo to yield a tan solid which was recrystallized from 22 L of 21:1 carbon tetrachloride/ethanol. The resulting white crystals are collected by vacuum filtration.

Ethyl 4-amino1-methylimidazole-2-carboxylate hydrochloride

Ethyl 1-methyl-4-nitroimidazole-2-carboxylate (103 g, 520 mmol) was dissolved in 5 L of 1:1 ethanol/ethyl acetate. 20 g 10% Pd/C slurried in 500 mL ethyl acetate was added and the mixture stirred under a slight positive pressure of hydrogen (c.a. 1.1 atm) for 48 h. The reaction mixture was filtered, concentrated in vacuo to a volume of 500 mL and 5 L of cold anhydrous ethyl ether added. Addition of HCl gas provided a white precipitate. The solution was cooled at −20° C. for 4 h and the precipitate collected by vacuum filtration and dried in vacuo to provide (75 g, 78% yield) of a fine white powder.

4-[(tert-butoxycarbonyl)amino]-1-methylimidazole-2-carboxylic acid

Ethyl 4-amino-1-methylimidazole-2-carboxylate hydrochloride (75 g, 395 mmol) was dissolved in 200 mL DMF. DIEA (45 mL, 491 mmol) was added followed by di-t-butyldicarbonate (99 g, 491 mmol). The mixture was shaken at 60° C. for 18 h, allowed to assume room temperature, and partitioned between 500 mL brine, 500 mL ethyl ether. The ether layer was extracted with (2×200 mL each) 10% citric acid, brine, satd. sodium bicarbonate and brine, dried over sodium sulfate and concentrated in vacuo to yield the Boc-ester contaminated with 20% Boc-anhydride as indicated by $^1$H NMR. The Boc-ester, used without further purification, was dissolved in 200 mL 1 M NaOH. The reaction mixture was allowed to stand for 3 h at 60° C. with occasional agitation. The reaction mixture was cooled to 0° C., and carefully neutralized with 1 M HCl to pH 2, at which time a white gel formed. The gel was collected by vacuum filtration, frozen before drying, and remaining water lyophilized to yield a white powder.

4-[(tert-butoxycarbonyl)amino]-1-methylpyrrole-2-(4carboxamide-methyl imidazole)-2-carboxylic acid This compound was prepared as described below for (-[(tert-butoxycarbonyl)amino]-butyric acid -(4-carboxamido-1-methyl-imidazole)-2-carboxylic acid, substituting Boc-Pyrrole acid for Boc-(-aminobutyric acid. (4.1 g, 91% yield).

(γ-[(tert-butoxycarbonyl)amino]-butyric acid-(4-carboxamido-1-methyl-imidazole)-2-carboxylic acid To a solution of Boc-(-aminobutyric acid (10 g, 49 mmol) in 40 mL DMF was added 1.2 eq HOBt (7.9 g, 59 mmol) followed by 1.2 eq DCC (11.9 g, 59 mmol). The solution was stirred for 24 h, and the DCU removed by filtration. Separately, to a solution of ethyl 4-nitro-1-methylimidazole-2-carboxylate (9.8 g, 49 mmol) in 20 mL DMF was added Pd/C catalyst (10%, 1 g), and the mixture was hydrogenated in a Parr bomb apparatus (500 psi H2) for 2 h. The catalyst was removed by filtration through celite and filtrate immediately added to the HOBt ester solution. An excess of DIEA (15 mL) was then added and the reaction stirred at 37° C. for 48 h. The reaction mixture was then added dropwise to a stirred solution of ice water and the resulting precipitate collected by vacuum filtration to provide crude ethyl 4-[[[3-[(tert-butoxycarbonyl]amino]propyl]carbonylamino]-1-methylimidazole-2-carboxylate (5 g, 14.1 mmol). To the crude ester dissolved in 50 mL methanol was added 50 mL 1M KOH and the resulting mixture allowed to stir for 6 h at 37° C. Excess methanol was removed in vacuo and the resulting solution acidified by the addition of 1 M HCl. The resulting precipitate was collected by vacuum filtration and dried in vacuo to yield a brown powder. (4.4 g, 89% yield).

Solid Phase Syntheses

Activation of Imidazole-2-carboxylic acid, (γ-aminobutyric acid, Boc-glycine, and Boc-β-alanine. The appropriate amino acid or acid (2 mmol) was dissolved in 2 mL DMF. HBTU (720 mg, 1.9 mmol) was added followed by DIEA (1 mL) and the solution lightly shaken for at least 5 min.

Activation of Boc-Imidazole acid

Boc-imidazole acid (257 mg, 1 mmol) and HOBt (135 mg, 1 mmol) were dissolved in 2 mL DMF, DCC (202 mg, 1 mmol) is then added and the solution allowed to stand for at least 5 min.

Activation of Boc-(Imidazole acid and Boc-Pyrrole-Imidazole acid

The appropriate dimer (1 mmol) and HBTU (378 mg, 1 mmol) are combined in 2 mL DMF. DIEA (1 mL) is then added and the reaction mixture allowed to stand for 5 min.

Activation of Boc-Pyrrole acid (for coupling to Imidazole amine)

Boc-Pyrrole acid (514 mg, 2 mmol) was dissolved in 2 mL dichloromethane, DCC (420 mg, 2 mmol) added, and the solution allowed to stand for 10 min, DMAP (101 mg, 1 mmol) was added and the solution allowed to stand for 1 min.

Acetylation Mix 2 mL DMF, DIEA (710 µL, 4.0 mmol), and acetic anhydride (380 µL, 4.0 mmol) were combined immediately before use.

Manual Synthesis Protocol

Boc-β-alanine-Pam-Resin (1.25 g, 0.25 mmol) is placed in a 20 mL glass reaction vessel, shaken in DMF for 5 min and the reaction vessel drained. The resin was washed with DCM (2×30 s.) and the Boc group removed with 80% TFA/DCM/0.5 M PhSH, 1×30 s., 1×20 min. The resin was washed with DCM (2×30 s.) followed by DMF (1×30 s.). A resin sample (5–10 mg) was taken for analysis. The vessel was drained completely and activated monomer added, followed by DIEA if necessary. The reaction vessel was shaken vigorously to make a slurry. The coupling was allowed to proceed for 45 min, and a resin sample taken. The reaction vessel was then washed with DCM, followed by DMF.

Machine-Assisted Protocols

Machine-assisted synthesis was performed on a ABI 430A synthesizer on a 0.18 mmol scale (900 mg resin; 0.2 mmol/gram). Each cycle of amino acid addition involved: deprotection with approximately 80% TFA/DCM/0.4 M PhSH for 3 minutes, draining the reaction vessel, and then deprotection for 17 minutes; 2 dichloromethane flow washes; an NMP flow wash; draining the reaction vessel; coupling for 1 hour with in situ neutralization, addition of dimethyl sulfoxide (DMSO)/NMP, coupling for 30 minutes, addition of DIEA, coupling for 30 minutes; draining the reaction vessel; washing with DCM, taking a resin sample for evaluation of the progress of the synthesis by HPLC analysis; capping with acetic anhydride/DIEA in DCM for 6 minutes; and washing with DCM. A double couple cycle is employed when coupling aliphatic amino acids to imidazole, all other couplings are performed with single couple cycles.

The ABI 430A synthesizer was left in the standard hardware configuration for NMP-HOBt protocols. Reagent positions 1 and 7 were DIEA, reagent position 2 was TFA/0.5 M thiophenol, reagent position 3 was 70% ethanolamine/methanol, reagent position 4 was acetic anhydride, reagent position 5 was DMSO/NMP, reagent position 6 was methanol, and reagent position 8 was DMF. New activator functions were written, one for direct transfer of the cartridge contents to the concentrator (switch list 21, 25, 26, 35, 37, 44), and a second for transfer of reagent position 8 directly to the cartridge (switch list 37, 39, 45, 46).

Boc-Py-OBt ester (357 mg, 1 mmol) was dissolved in 2 mL DMF and filtered into a synthesis cartridge. Boc-Im acid monomer was activated (DCC/HOBt), filtered, and placed in a synthesis cartridge. Imidazole-2-carboxylic acid was added manually. At the initiation of the coupling cycle the synthesis was interrupted, the reaction vessel vented and the activated monomer added directly to the reaction vessel through the resin sampling loop via syringe. When manual addition was necessary an empty synthesis cartridge was used. Aliphatic amino acids (2 mmol) and HBTU (1.9 mmol) were placed in a synthesis cartridge. 3 mL of DMF was added using a calibrated delivery loop from reagent bottle 8, followed by calibrated delivery of 1 mL DIEA from reagent bottle 7, and a 3 minute mixing of the cartridge.

The activator cycle was written to transfer activated monomer directly from the cartridge to the concentrator vessel, bypassing the activator vessel. After transfer, 1 mL of DIEA was measured into the cartridge using a calibrated delivery loop, and the DIEA solution combined with the activated monomer solution in the concentrator vessel. The activated ester in 2:1 DMF/DIEA was then transferred to the reaction vessel. All lines were emptied with argon before and after solution transfers.

ImPyPy-γ-ImPyPy-β-alanine-Dp

ImPyPy-(-PyPyPy-β-alanine-Pam-Resin was prepared by machine-assisted synthesis protocols. A sample of resin (1 g, 0.17 mmol) was placed in a 20 mL glass scintillation vial, 4 mL of dimethylaminopropylamine added, and the solution heated at 55° C. for 18 h. Resin is removed by filtration through a disposable propylene filter and 16 mL of water added. The polyamide/amine mixture was purified directly by preparatory HPLC and the appropriate fractions lyophilized to yield a white powder.

Stepwise HPLC analysis

A resin sample (c.a. 4 mg) was placed in a 4 mL glass test tube, 200 :L of N,N-dimethylaminopropylamine was added and the mixture heated at 100° C. for 5 min. The cleavage mixture was filtered and a 25 :L sample analyzed by analytical HPLC at 254 nm.

EXAMPLE 2

β-alanine and γ-aminobutyric acid are turn and overlapped specific "guide" amino acids which may be combined predictably within the same molecule.[2]

hu 2Tranger et al, Chemistry and Biology, 1996, 3, 369–377.

Synthesis of Polyamides ImPyPy-γ-aminobutyric acid-ImPyPy-β-alanine-Dp and ImPyPy-γ-aminobutyric acid-ImPyPy-β-alanine-PyPyPy-G-Dp All polyamides were prepared in high purity using solid phase synthetic methodology as described above. Polyamides were assembled in a stepwise manner on Boc-β-alanine-Pam resin and Boc-glycine-Pam-resin respectively. Polyamides ImPyPy-γ-aminobutyric acid-ImPyPy-β-alanine-Dp, ImPyPy-γ-aminobutyric acid-ImPyPy-β-alanine-PyPyPy-G-Dp and ImPyPy-γ-aminobutyric acid-ImPyPy-β-alanine-PyPyPy-G-Dp-NH$_2$ were cleaved from the support with an appropriate primary amine and purified by reversed-phase HPLC to provide 10–30 mg of polyamide. A primary amine group suitable for post-synthetic modification can be provided. Amine modified polyamides are treated with an excess of the dianhydride of EDTA, unreacted anhydride hydrolyzed, and the EDTA modified polyamide ImPyPy-γ-aminobutyric acid-ImPyPy-β-alanine-PyPyPy-G-Dp-EDTA isolated by reversed-phase HPLC. Polyamides were cleaved from the support.

ImPyPy-γ-aminobutyric acid-ImPyPy-β-alanine-PyPyPy-G-Dp-NH$_2$

Polyamide was prepared by machine-assisted solid phase methods as a white powder (29 mg, 59% recovery).

ImPyPy-γ-aminobutyric acid-ImPyPy-β-alanine-PyPyPy-G-Dp-EDTA

EDTA-dianhydride (50 mg) was dissolved in 1 mL DMSO/NMP solution and 1 mL DIEA by heating at 55° C. for 5 min. The dianhydride solution was added to ImPyPy-γ-aminobutyric acid-ImPyPy-β-alanine-PyPyPy-G-Dp-NH$_2$ (9.0 mg, 5 μmol) dissolved in 750 μL DMSO. The mixture was heated at 55° C. for 25 min, treated with 3 mL 0.1 M NaOH, and heated at 55° C. for 10 min. 0.1% TFA was added to adjust the total volume to 8 mL and the solution purified directly by reversed-phase HPLC to provide ImPyPy-γ-aminobutyric acid-ImPyPy-β-alanine-PyPyPy-G-Dp-EDTA as a white powder (3 mg, 30% recovery after HPLC purification).

Preparation of $^{32}$P-labeled DNA

Plasmid pJT8 was prepared by hybridizing two sets of 5'-phosphorylated complementary oligonucleotides,
5'-CCGGGAACGTAGCGTACCGGTCGCAAAAAGAC AGGCTCGA-3', and
5'-GGCGTCGAGCCTGTCTTTTTGCGACCGGTACGC TACGTTC-3', and
5'-CGCCGCATATAGACAGGCCCAGCTGCGTCCTAG TAGCGTCGTAGCGT CTTAAGAG-3' and
5'-TCGACTCTTAAGACGCTACGACGCTAGCTAGGA CGCAGCTGGGCCTGT CTATATGC-3', and ligating the resulting duplexes to the large pUC19 AvaI/SalI restriction fragment. The 3'-$^{32}$P end-labeled AflII/FspI fragment was prepared by digesting the plasmid with AflII and simultaneously filling in using Sequenase, ["-$^{32}$P]-deoxyadenosine-5'-triphosphate, and ["-$^{32}$P]-thymidine-5'-triphosphate, digesting with FspI, and isolating the 247 bp fragment by nondenaturing gel electrophoresis. The 5'-$^{32}$P-end-labeled AflII/FspI fragment was prepared using standard methods. A and G sequencing were carried out as described.[3] Standard methods were used for all DNA manipulations.[4]

[3] Maxam & Gilbert, Methods Enzymol., 1980, 65, 499–560; Iverson & Dervan, Methods Enzymol., 1987, 15, 7823–7830; Sambrook et al, 1989, Molecular Cloning, 2nd ed., Cold Spring Harbor Laboratory Press: Cold Spring Harbor, N.Y.
[4] Sambrook et al, 1989, Molecular Cloning, 2nd ed., Cold Spring Harbor Laboratory Press: Cold Spring Harbor, N.Y.

Affinity Cleavage Reactions

All reactions were executed in a total volume of 400 mL. A stock solution of EDTA-modified polyamide or H$_2$O was added to a solution containing labeled restriction fragment (15,000 cpm), affording final solution conditions of 20 mM HEPES, 200 mM NaCl, 50 mg/mL glycogen, and pH 7.3. Subsequently, 20 μL of freshly prepared 20 mM Fe(NH4)$_2$(SO$_4$)$_2$ was added and the solution allowed to equilibrate for 20 min. Cleavage reactions were initiated by the addition of 40 μ of 50 mM dithiothreitol, allowed to proceed for 12 min at 22° C., then stopped by the addition of 1 mL of ethanol. Reactions were precipitated and the cleavage products separated using standard methods. Next, 10 μL of a solution containing calf thymus DNA (140 mM base-pair) (Pharmacia) and glycogen (2.8 mg/mL) was added, and the DNA precipitated. The reactions were resuspended in 1× TBE/80% formamide loading buffer, denatured by heating at 85° C. for 10 min, and placed on ice. The reaction products were separated by electrophoresis on an 8% polyacrylamide gel (5% crosslink, 7 M urea) in 1×TBE at 2000 V. Gels were dried and exposed to a storage phosphor screen. Relative cleavage intensities were determined by volume integration of individual cleavage bands using ImageQuant software.

Quantitative DNase I Footprint Titration Experiments

All reactions were executed in a total volume of 400 μL. A polyamide stock solution or H$_2$O (for reference lanes) was added to an assay buffer containing radiolabeled restriction fragment (15,000 cpm), affording final solution conditions of 10 mM TrisHCl, 10 mM KCl, 10 mM MgCl$_2$, 5 mM CaCl$_2$, pH 7.0, and either (i) 1 pM–10 nM polyamide or (ii) no polyamide (for reference lanes). The solutions were allowed to equilibrate at 22° C. for (i) 12 h for polyamide 1 or (ii) 36 h for polyamide 2. Footprinting reactions were initiated by the addition of 10 mL of a DNase I stock solution (at the appropriate concentration to give ⁻55% intact DNA) containing 1 mM dithiothreitol and allowed to proceed for seven min at 22° C. The reactions were stopped by the addition of 50 μL of a solution containing 2.25 M NaCl, 150 mM EDTA, 0.6 mg/mL glycogen, and 30 mM base-pair calf thymus DNA, and ethanol precipitated. Reactions were resuspended in 1× TBE/80% formamide loading buffer, denatured by heating at 85° C. for 10 min, and placed on ice. The reaction products were separated by electrophoresis on an 8% polyacrylamide gel (5% crosslink, 7 M urea) in 1× TBE at 2000 V. Gels were dried and exposed to a storage phosphor screen (Molecular Dynamics).

Quantitation and Data Analysis

Data from the footprint titration gels were obtained using a Molecular Dynamics 400S PhosphorImager followed by quantitation using ImageQuant software (Molecular Dynamics). Background-corrected volume integration of rectangles encompassing the footprint sites and a reference site at which DNase I reactivity was invariant across the titration generated values for the site intensities ($I_{site}$) and the reference intensity ($I_{ref}$). The apparent fractional occupancy ($2_{spp}$) of the sites were calculated using the equation (1):

$$Q_{app} = 1 - \frac{I_{site}/I_{ref}}{I^{\circ}_{site}/I^{\circ}_{ref}} \quad (1)$$

where $I^{\circ}_{site}$ and $I^{\circ}_{ref}$ are the site and reference intensities, respectively, from a control lane to which no polyamide was added. The ($[L]_{tot}$, $2_{spp}$) data points were fit to a general Hill equation (eq 2) by minimizing the difference between $2_{spp}$ and $2_{fit}$:

$$Q_* = Q_{\min} + (Q_{\max} - Q_{\min})\frac{K_a^*[L]_{tot}^*}{1 + K_a^*[L]_{tot}^*} \quad (2)$$

where $[L]_{tot}$ is the total polyamide concentration, $K_s$ is the equilibrium association constant, and $2_{min}$ and $2_{max}$ are the experimentally determined site saturation values when the site is unoccupied or saturated, respectively. The data were fit using a nonlinear least-squares fitting procedure with $K_a$, $2_{max}$, and $2_{min}$ as the adjustable parameters. For polyamide ImPyPy-γ-aminobutyric acid-ImPyPy-β-alanine-Dp, binding isotherms for the 5'-AGACA-3' target sites were adequately fit by Langmuir isotherms (eq 2, n=1), consistent with formation of 1:1 polyamide-DNA complexes. For ImPyPy-γ-aminobutyric acid-ImPyPy-β-alanine-PyPyPy-G-Dp, steeper binding isotherms (eq 2, n=1.8–2.2) were observed at the target sites 5'-AAAAAGACA-3' and 5'-ATATAGACA-3'. The steepness of these isotherms may be due to the very high equilibrium association constants at these sites. Treatment of the data in this manner does not represent an attempt to model a binding mechanism. The data is a comparison of values of the apparent first-order association constant, a value that represents the concentration of ligand at which a site is half-saturated. The binding isotherms were normalized using the following equation:

$$Q_{norm} = \frac{Q_{app} - Q_{min}}{Q_{max} - Q_{min}} \quad (3)$$

Four sets of data were used in determining each association constant. The method for determining association constants used here involves the assumption that $[L]_{tot} \cdot [L]_{free}$, where $[L]_{free}$ is the concentration of polyamide free in solution (unbound). For very high association constants this assumption becomes invalid, resulting in underestimated association constants. In the experiments described here, the DNA concentration is estimated to be ~5 pM. As a consequence, apparent association constants greater than ~$10^{10}$ M$^{-1}$ should be regarded as lower limits.

DNA-binding Orientation

Affinity cleavage[5] experiments with ImPyPy-γ-aminobutyric acid-ImPyPy-β-alanine-PyPyPy-G-Dp-EDTAFe(II) (2-Fe(II)) on the 5'- or 3'-$^{32}$P end-labeled 247 bp pJT4 AflII/FspI restriction fragment revealed that this polyamide selectively binds the 5'-AAAAAGACA-3' and 5'-ATATAGACA-3' target sequences at subnanomolar concentration. A single 3'-shifted cleavage pattern is observed at each 9 bp site indicating that the polyamide is bound in one orientation with the C-terminus at the 5' end of the 5'-AAAAAGACA-3' and 5'-ATATAGACA-3' sequences.

[5]Wade et al, J. Am. Chem. Soc., 1992 114, 8783–8794; Schultz et al, J. Am. Chem. Soc., 1982, 104, 6861–6863.

DNA-binding Affinity and Specificity

The exact locations and sizes of all binding sites were determined first by preliminary MPEFe(II) footprinting experiments.[6] Quantitative DNase I footprint titration experiments[7] on the 3'-$^{32}$P-labeled 247 bp restriction fragment (10 mM

[6]Hertzberg & Dervan, J. Am. Chem. Soc., 1982 104, 313–315.
[7]Fox & Waring, Nucleic Acids Res., 1984, 12, 9271–9285; Brenowitz et al, Methods Enzymol., 1986, 130, 132–181; Brenowitz, et al, Proc. Natl. Acad. Sci. U.S.A, 1986, 83, TrisHCl, 10 mM KCl, 10 mM MgCl$_2$, 5 mM CaCl$_2$, pH 7.0, 22° C.) reveal that ImPyPy-γ-aminobutyric acid-ImPyPy-β-alanine-PyPyPy-G-Dp specifically binds 5'-AAAAAGACA-3' and 5'-ATATAGACA-3' with equilibrium association constants of Ka=2×10$^{10}$ M$^{-1}$ and Ka=8×10$^9$ M$^{-1}$, respectively. Additional sites on the restriction fragment are bound with lower affinity. For comparison, the six-ring hairpin polyamide ImPyPy-γ-aminobutyric acid-ImPyPy-β-alanine-Dp binds 5'-aaaaAGACA-3' and 5'-atatAGACA-3' with association constants of Ka=5×10$^7$ M$^{-1}$ and Ka=9×10$^7$ M$^{-1}$, respectively.

Relative to the six-ring polyamide ImPyPy-γ-aminobutyric acid-ImPyPy-β-alanine-Dp, the nine-ring polyamide ImPyPy-γ-aminobutyric acid-ImPyPy-β-alanine-PyPyPy-G-Dp binds 5'-AAAAAGACA-3' and 5'-ATATAGACA-3' with ~400-fold and ~100-fold higher affinity, respectively. Similar binding enhancements have recently been reported in a separate system.[8] Addition of a C-terminal PyPyPy subunit using a β-alanine linker is an effective strategy for increasing the DNA-binding affinity of hairpin polyamides that bind adjacent to an (A,T)$_4$ sequence.

[8]Trauger et al., Nature, 1996, 382, 559–561

Polyamide ImPyPy-γ-aminobutyric acid-ImPyPy-β-alanine-PyPyPy-G-Dp binds several mismatch sites present on the 247 bp restriction fragment with high affinity. The two highest affinity mismatch sites, 5'-GAATTCACT-3' (K$_s$=4.5×10$^9$ M$^{-1}$) and 5'-GTTTTCCCA-3' (K$_a$=2.5×10$^9$ M$^{-1}$), are bound with at least 5-fold reduced affinity relative to the optimal match site 5'-AAAAAGACA-3' (formally mismatched base-pairs are highlighted), although this value may be a lower limit due to the uncertainty in the very high equilibrium association constant for the optimal match site. In contrast, the six-ring polyamide ImPyPy-γ-aminobutyric acid-ImPyPy-β-alanine-Dp binds more strongly to the match site 5'-AGACA-3' over the single base-pair mismatch sites 5'-ATTCA-3' and 5'-TTACA-3' by a factor of 10.

EXAMPLE 3

Subnanomolar ligand binding with single mismatch differentiation

The DNA-binding affinities were evaluated of two eight-ring hairpin polyamides, ImPyPyPy-γ-ImPyPyPy-β-Dp (1) and ImPyPyPy-γ-PyPyPyPy-β-Dp (2), which differ by a single amino acid, for two 6 base pair (bp) target sites, 5'-AGTACT-3' and 5'-AGTATT-3', which differ by a single base pair. Based on the pairing rules for polyamide-DNA complexes, the sites 5'-AGTACA-3' and 5'-AGTATT-3' are for polyamide 1 "match" and "single base pair mismatch" sites, respectively, and for polyamide 2 "single base pair mismatch" and "match" sites, respectively (FIG. 2).

Polyamides 1 and 2 were synthesized by solid phase methods and purified by reversed phase HPLC[9]. The identity and purity of the polyamides was verified by $^1$H NMR, MALDI-TOF MS, and analytical HPLC. MALDI-TOF MS: 1, 1223.4 (1223.3 calculated for M+H); 2, 1222.3 (1222.3 calculated for M+H). Equilibrium association constants for complexes of 1 and 2 with match and mismatch six base pair binding sites on a 3'-$^{32}$P-labeled 229 bp restriction fragment were determined by quantitative DNase I footprint titration experiments[10] (Table I).

TABLE 1

| | Equilibrium association constants (M$^{-1}$) | |
|---|---|---|
| Binding Site | 1 | 2 |
| 5'-ttAGTACTtg-3' | 3.7 × 10$^{10}$ (0.8) | 5.0 × 10$^8$ (0.5) |
| 5'-ttAGTATTtg-3' | 4.1 × 10$^8$ (0.5) | 3.5 × 10$^9$ (0.8) |

The reported association constants are the average values obtained from three DNase I footprint titration experiments. The standard deviation for each data set is indicated in parentheses. Assays were carried out in the presence of 10 mM Tris · HCl, 10 mM KCl, 10 mM MgCl$_2$, and 5 mM CaCl$_2$ at pH 7.0 and 22° C. The six base-pair binding sites are in capital letters, with flanking sequences in lower-case letters.

[9]Baird and Dervan, J. Am. Chem. Soc.,1996, 118, 6141–6146
[10]Galas & Schmitz, Nucleic Acids Res., 1978, 5 3157–3170; Fox & Waring, ibid, 1984, 12, 9271–9285; Brenowitz et al., Meth. Enzym. 1986, 130, 132–181

Polyamide 1 binds its match site 5'-AGTACT-3' at 0.03 nM concentration and its single base pair mismatch site 5'-AGTATT-3' with nearly 100-fold lower affinity. Polyamide 2 binds its designated match site 5'-AGTATT-3' at 0.3 nM concentration and its single base pair mismatch site 5'-AGTACT-3' with nearly 10-fold lower affinity. The specificity of 1 and 2 for their respective match sites results from very small structural changes. Replacing a single nitrogen atom in 1 with C-H (as in 2) reduces the affinity of the polyamide●5'-AGTACT-3' complex by ~75-fold representing a free energy difference of −2.5 kcal/mole. Similarly, replacing a C-H in 2 with N (as in 1) reduces the affinity of the polyamide●5'-AGTA7T-3' complex −10-fold, a loss in binding energy of −1.3 kcal/mol.

Quantitative DNase I footprint titration experiments with polyamides 1 and 2 on the 3'-$^{32}$P-labeled 229 bp pJT8 AflII/FspI restriction fragment. Comparison lanes were A and G sequencing lanes; DNase I digestion products obtained in the absence of polyamide; DNase I digestion products obtained in the presence of 1 pM, 2 pM, 5 pM, 10 pM, 15 pM, 25 pM, 40 pM, 65 pM, 0.1 nM, 0.15 nM, 0.25 nM, 0.4 nM, 0.65 nM, 1 nM, 2 nM, 5 nM, and 10 nM polyamide, respectively; and intact DNA. Polyamide binding sites for which association constants were determined for 5'-AGTACT-3' and 5'-AGTATT-3'. Additional sites not analyzed were 5'-TGTAAA-3', 5'-TGTGCT-3', and 5'-TAAGTT-3'. All reactions were executed in a total volume of 400 µL. A polyamide stock solution or H$_2$O was added to an assay buffer containing radiolabeled restriction fragment, affording final solution conditions of 10 mM Tris●HCl, 10 mM KCl, 10 mM MgCl$_2$, 5 mM CaCl$_2$, and pH 7.0. The solutions were allowed to equilibrate for 12–15 h at 22° C. prior to initiation of footprinting reactions. Footprinting reactions, separation of cleavage products, and data analysis were carried out as described elsewhere[11]. Plasmid pJT8 was prepared by hybridizing two 5'-phosphorylated complementary oligonucleotides, 5'-CCGGTTAG-TATTTGGATGGGCCTGGTTAGTACTTG-GATGGGAGACCGCCTGGGAATACCAGGTGTCGTA TCTTAAGAG-3'

[11]Mrkisch et al., J. Am. Chem. Soc., 1994, 116, 7983–7989 and 5'-TC-GACTCTTAAGATACGACACCTGGTATTC-CCAGGCGGTCTCCCATCCAAGTACTAAC-CAGGCCCATCCAAATACTAA-3', and ligating the resulting duplex to the large pUC19 AvaI/SalI restriction fragment.

EXAMPLE 4

Intracellular binding and transcription inhibition Methods
Polyamides. Polyamides were synthesized by solid phase methods.[13] The identity and purity of the polyamides was verified by $^1$H NMR, matrix assisted laser desorption/ionization time of flight mass spectrometry (MALDI-TOF-MS), and anlaytical HPLC. MALDI-TOF-MS: 1, 1223.4 (1223.3 calcd for M+H); 2, 1222.3 (1222.3 calcd for M+H); 3, 1223.1 (1223.3 calcd for M+H).

Transcription inhibition in vitro. A high speed cytosolic extract from unfertilized Xenopus egges was prepared as decribed.[14] DNA templates for transcription were the somatic-type 5S RNA gene contained in plasmid pXlsll[15] (50 ng per reaction)and the tyrD tRNA gene contained in plasmid pTyrD[16] (100 ng plasmid DNA per reaction), both from X. laevis. Transcription reactions (20 µL final volume) contained the following components: 2.5 µL extract 9 ng (12 nM) of TFIIIA isolated from immature oocytes[17], 0.6 mM ATP, UTP, CTP,0.02 mM GTP and 10 µCi of [α-$^{32}$P] GTP and the final buffer components 12 mM HEPES (pH 7.5), 60 mM KCl, 6 mM MgCl$_2$, 25 µM ZnCl$_2$, and 8% (v/v) glycerol. Plasmid DNAs were preincubated with polyamides in the same buffer prior to adding TFIIIA and other reaction components. RNA was pruified and analyzed on a denaturing 6% polyacrylamide gel. A Molecular Dynamics Phosphorimager equipped with ImageQuant software was used to quantify the effect of the polyamides on 5S and tRNA gene transcription.

[13]Baird, E. E. and Dervan, P. B., J. Am. Chem. Soc. 118, 6141–6146 (1996)
[14]Hartl, P. et al., J Cell Biol. 120, 613–624 (1993)
[15]Peterson, R. C. et al., Cell 20, 131–144 (1980)
[16]Stutz, F. et al., Genes Dev. 3, 1190–1198 (1989)
[17]Smith, D. R. et al., Cell 37, 645–652 (1984)

Transcription inhibition in vivo. Fibroblasts from a Xenopus kidney derived cell line (kindly provided by Dr. P. Labhart, Scripps) were grown at ambient temperature in 25 cm$^2$ culture flasks in Dulbecco's modified Eagle medium containing 10% (v/v) fetal calf serum. Cells were passaged for a minimum of three days prior to the addiiton of polyamide to the culture medium. Incubations were continued for various times and nuclei were prepared by hypotonic lysis and used as templates for transcription as described.[18] DNA content was determined by measuring the absorbance of an aliquot of the isolated nuclei in 1% (w/v) sodium dodecyl sulfate (using an extinction coefficient at 260 nM of 1 AU=50 µg/mL DNA). The buffer components and labeled and unlabeled nucleoside triphosphates were as for the plasmid transcription reactions. Reactions were supplemented with 2 µL of RNA polymerase III (at approximately 50 µg/mL)isolated from Xenopus oocytes.[19]

[18]Schlissel, M. S. and Brown, D. D., Cell 37, 903–913 (1984)
[19]Roeder, R. G., J. Biol. Chem. 258, 1932–1941 (1983)

Results

The effect of polyamide 1 (ImPyPyPy-γ-ImPyPyPy-β-Dp) on TFIIIA binding to a restriction fragment isolated from a 5S RNA gene-containing plasmid was examinded. Zfl-3, a recombinant TFIIIA analog missing fingers 4–9, binds in the major groove of the C-block promoter element (see FIG. 1). DNase I footprinting demonstrates that zfl-3 and polyamide 1 can co-occupy the same DNA molecule. When 5 nM polyamide 1 was preincubated with the same DNA target, the binding of nine finger TFIIIA was inhibited by >90%. The differential inhibition of zfl-3 and full-length TFIIIA provides evidence that finger 4 interacts with or is placed in the minor groove. Polyamide 1 does not inhibit TFIIIA binding to 5S RNA.

Transcription of the 5S RNA gene in an in vitro system was monitored in the presence of increasing concentrations (10–60 nM) of polyamide 1. In these experiments, polyamide 1 was added to a 5S RNA gene containing plasmid prior to the addition of exogenous TFIIIA (12 nM) and a crude extract derived from unfertilized Xenopus eggs. As a control, a tyrosine tRNA gene was included on a separate plasmid in these reactions. The tRNA gene has an upstream binding site for 1, but lacks a predicted protein-polyamide interaction. Both genes are actively transcribed in this system, either individually or in mixed template reactions. Addition of 60 nM polyamide 1 inhibits 5S gene transcription by >80%. Only a small degree of non-specific inhibition of tRNA transcription is observed at the concentrations of polyamide 1 required for efficient 5S RNA inhibition. The targeted 5S RNA gene is inhibited approximately 10-fold more effectively than the control tRNA gene. Mismatch polyamides 2 (ImPyPyPy-γ-PyPyPyPy-β-Dp) and 3 (ImPyImPy-γ-PyPyPyPy-β-Dp) do not inhibit 5S RNA transcription at concentrations up to 60 nM. If the TFIIIA-DNA complex is first allowed to form, 30 nM polyamide 1 added, and the mixture incubated for 90 minutes prior to adding egg extract, efficient inhibition (80%) of 5S RNA transcription is also observed. Shorter incubation times result in less inhibition. The required incubation time of 90 minutes is similar to the measured half-life of the TFIIIA-DNA complex and supports that polyamide 1 forms a more stable complex with DNA than does TFIIIA.

The effect of the polyamides on 5S gene transcription in vivo was monitored. Xenopus kidney-derived fibroblasts were grown in the presence of increasing concentrations of polyamide 1 in the culture medium for various times. We found that concentrations of polyamide up to 1 µM were not toxic, as measured by cell density, if growth was limited to less than 72 hours. Nuclei were prepared from cells by hypotonic lysis and equivalent amounts of the isolated nuclei from control and treated cells were used as templates for transcription with exogenous RNA polymerase III and labeled and unlabeled nucleoside triphosphates. This expermiment monitors the occupancy of class III genes with active transcription complexes.[20] 5S RNA transcription can easily be asessed since the repetitive 5S genes give rise to a prominent band on a denaturing polyacrylamide gel. An autoradiogram was taken of the gel and the following observations made based on the observed autoradiogram.

[20]Schlissel, M. S., Cell, supra

Concentrations of polyamide 1 as low as 100 nM have a pronounced and selective effect on 5S transcription. At higher polyamide concentration, a general decrease in the transcriptional activity of the nuclei is observed; however, at each concentration tested, the effects of the polyamide are much greater on 5S RNA transcrption than on tRNA transcription. Having established that nearly maximal inhibition of 5S transcription is achieved with 1 $\mu$M polyamide 1, we monitored nuclear transcription after various times of cell growth in the presence of the polyamide. No inhibition is observed for zero time incubation with polyamide 1 at 1 FM concentration, indicating that disruption of transcription complexes does not occur during or after the isolation or work-up of cell nuclei. Statistically equivalent levels of 5S transcription were observed when the cells were exposed to polyamide 1 for 24, 48 or 72 hours.

The observations support the conclusion that polyamide 1 is able to enter cells, transit to the nucleus and disrupt transcription complexes on the chromosomal 5S RNA genes. To rule out the possibility that the observed inhibitio is due to some non-specific toxicity of the polyamide rather than to direct binding to the 5S RNA gene, the effects of mismatch polyamides 2 and 3 in the nuclear transcription assay were monitored. Only a small effect on 5S RNA synthesis relative to tRNA synthesis is observed with 1 $\mu$M of the mismatch polyamides 2 or 3 in the culture medium for 24 hours. This result indicates that the general inhibition of transcription observed with high concentrations of polyamide 1 may be a secondary effect of the inhibition of 5S RNA synthesis in vivo, rather than the result of non-specific polyamide interactions. Polyamide 2 affects a small enhancement of 5S RNA transcription in vitro and in vivo, indicating that polyamides may be able to upregulate transcription in certain cases.

As evidenced by the above results, the subject invention provides novel compounds, which are oligomers of organic cyclic groups, particularly azoles, where the compounds fit in the minor groove of dsDNA and provide for hydrogen bonding, polar interactions, and van der Waal's interactions resulting in high affinities and high association constants.

The subject compositions provide for substantial differentiation between the target sequence and single mismatch sequences. Normally, there will be at least a two-fold difference between the two sequences, more usually at least a five-fold difference, and preferentially at least a ten-fold difference or greater. In this way, one can insure that the target sequence will be primarily affected, with little effect on other sequences. Normally, the target sequence will be at least five nucleotides, usually at least six nucleotides, more usually at least eight nucleotides, and not more than about twenty nucleotides. By using combinations of compositions, where the combinations bind to different sequences, which may be proximal to each other, one may further enhance the inhibition at a particular gene.

The subject compositions are shown to bind with high affinities to specific dsDNA sequences and with substantially lower affinities to single base mismatches. In this way, even in complex compositions of dsDNA, such as may be encountered in cellular compositions, there is substantial assurance that the target sequence will be affected and other sequences will be little affected, if at all. Furthermore, the subject compositions are capable of transport across a cellular membrane and through the cytosol to the nucleus. The subject compositions are capable of binding to chromosomal dsDNA involved with nucleosomes and inhibit transcription of genes which form complexes with the subject compositions. Single oligomers may be employed or combinations of oligomers to provide for the desired complex formation. By using the subject compositions in diagnosis, one is not required to melt the DNA to provide for single-stranded DNA. Rather, the subject compositions can accurately target the dsDNA and avoid the melting and competition between the natural strands and the labeled complementary strand, as is employed conventionally today. The subject compositions may be used for cleavage of dsDNA at specific sites, so as to isolate target DNA, which may then be readily amplified using PCR. By further modifying the subject compositions, one may further expand their applications in their use for identifying sequences, cleaving specific sequences, investigating the role of genes, screening for the presence of sequences in cells, and inhibiting proliferation of cells.

The references described throughout this specification are fully incorporated by reference.

Having now fully described the invention, it will be apparent to one of ordinary skill in the art that many changes and modifications can be made thereto without departing from the spirit or scope of the invention as set forth herein.

What is claimed is:

1. A cell comprising dsDNA to which is bound in the minor groove at a target site from 1 to 2 oligomers, where the oligomers are selected to provide specific binding to said dsDNA at said target site, each of said oligomers comprising organic cyclic groups of from 5 to 6 annular members, where at least 60% of the groups are heterocycles having from 1 to 3 heteroatoms, where the heteroatoms are nitrogen, oxygen and sulfur, and wherein at least 60% of the heterocycles have at least one nitrogen atom, and said heterocycles are linked by chains of 2 atoms, wherein at least some of the chains have NH, wherein at least one of said oligomers has at least 7 of said nitrogen containing heterocycles, where at least one of said heterocycles is specific for A, G, C or T, and a pair of heterocycles refers to two heterocycles paired to a complementary pair of nucleotides in said dsDNA, each oligomer comprising at least two units of 2 consecutive heterocycles which form, at the target sites, intramolecular pairs of heterocycles with itself or intermolecular pairs of heterocycles with another oligomer, where when an oligomer forms intramolecular pairs, said oligomer comprises an internal molecule which shifts the spacing of the heterocycles or forms a hairpin turn, and when two oligomers form intermolecular pairs, each oligomer comprises an internal aliphatic amino acid of from 2 to 6 carbon atoms, where said internal aliphatic amino acid is paired with an A or T; and each of said oligomers comprising at at least one terminus, an aliphatic amino acid of from 2 to 6 carbon atoms or an alkyl chain comprising a polar group 2 to 4 carbon atoms from the bond linking said alkyl chain to the remainder of each oligomer, where each oligomer has one or more hydrogen atoms away from the surface of said minor groove which may be substituted, wherein the total number of carbon atoms of substituents is not more than 100 carbon atoms.

2. A cell according to claim 1, wherein said cell is a mammalian cell.

3. A cell comprising dsDNA to which is bound in the minor groove at a target site from 1 to 2 oligomers of N-heterocycles consisting of N-methyl pyrrole (Py) and N-methyl imidazole (Im), where the oligomers are selected to provide specific binding to said dsDNA at said target site,
wherein at least one of said oligomers comprises at least 7 said heterocycles, where the pairing of heterocycles in relation to said target dsDNA is defined as Im/Py to G/C, Py/Im to C/G, and Py/Py to A/T and T/A and a pair of heterocycles refers to two heterocycles that are paired to a complementary pair of nucleotides in said dsDNA, and said heterocycles are linked by chains of 2 atoms, wherein at least some of the chains have NH,
each oligomer comprising at least two units of consecutive heterocycles which form, at target sites, intramolecular pairs of heterocycles with itself or intermolecular pairs of heterocycles with another oligomer,
where when an oligomer forms intramolecular pairs, said oligomer comprises an internal molecule γ-aminobutyric acid, and
when two oligomers form intermolecular pairs, each oligomer comprises an internal β-alanine, said internal β-alanine is paired with an A or T;
where each oligomer terminates, at one or both termini, in a glycine or β-alanine amino acid joined to an alkyl chain of from 2 to 4 carbon atoms comprising a polar group, with the proviso that a γ-aminobutyric acid may join the termini to circularize an oligomer,
where each oligomer has one or more hydrogen atoms away from the surface of said minor groove which may be substituted, wherein the total number of carbon atoms of substituents is not more than 30 carbon atoms.

4. A cell according to claim 3, wherein said chains of 2 atoms are amido groups.

5. A cell according to claim 3, wherein one oligomer at target sites with two oligomers have one β-alanine separating units of at least 2 N-heterocycles.

6. A cell according to claim 3, wherein in said oligomers there are not more than 3 consecutive Ims.

7. A cell according to claim 3, wherein one oligomer at target sites with two oligomers comprises at least 8 N-heterocycles.

8. A cell according to claim 3, wherein one oligomer at target sites with two oligomers comprises at least 2 unpaired N-heterocycles.

9. A cell according to claim 3, wherein the oligomers are free of substituents.

10. A cell according to claim 3, wherein each oligomer may be substituted on said polar group comprising alkyl chain.

11. A cell according to claim 1, wherein each oligomer may be substituted on said polar group comprising alkyl chain.

12. A cell according to claim 7, wherein said oligomer comprises at least 2 unpaired N-heterocycles.

13. A cell comprising dsDNA to which is bound in the minor groove at a target site from 1 to 2 oligomers of N-heterocycles consisting of N-methyl pyrrole (Py) and N-methyl imidazole (Im), where the oligomers are selected to provide specific binding to said dsDNA at said target site,
wherein each of said oligomers is of not more than 5 kD and at least one oligomer comprises at least 7 said heterocycles, where the pairing of heterocycles in relation to said target dsDNA is defined as Im/Py to G/C, Py/Im to C/G, and Py/Py to A/T and T/A and a pair of heterocycles refers to two heterocycles that are paired to a complementary pair of nucleotides in said dsDNA, and said heterocycles are linked by chains of 2 atoms, wherein at least some of the chains have NH,
each oligomer comprising at least two units of consecutive heterocycles which form, at target sites, intramolecular pairs with itself or intermolecular pairs with another oligomer,
where when an oligomer forms intramolecular pairs, said oligomer comprises an internal molecule γ-aminobutyric acid, and
when two oligomers form intermolecular pairs, each oligomer comprises an internal β-alanine, said internal β-alanine is paired with an A or T;
where each oligomer terminates, at one or both termini, in a glycine or β-alanine amino acid joined to an alkyl chain of from 2 to 4 carbon atoms comprising a polar group, with the proviso that a γ-aminobutyric acid may join the termini to circularize an oligomer and
where each oligomer has one or more hydrogen atoms away from the surface of said minor groove which may be substituted, wherein the total number of carbon atoms of substituents is not more than 30 carbon atoms.

14. A cell according to claim 13, wherein said oligomer is bound to a gene comprising a regulatory sequence and a coding sequence, wherein said gene has a level of transcription below the normal level.

15. A cell according to claim 13, wherein binding of said oligomers is at a $K_a$ of not less than about $10^9$ $M^{-1}$.

16. A cell according to claim 13, wherein said dsDNA is a chromosome which comprises a copy of a virus, and said oligomer is bound to a viral gene comprising a regulatory region and a coding region.

17. A cell comprising dsDNA to which is bound in the minor groove at a target site an oligomer of N-heterocycles consisting of N-methyl pyrrole (Py) and N-methyl imidazole (Im), where said oligomer is selected to provide specific binding to said dsDNA at said target site, at a $K_a$ of not less than about $10^9$ $M^{-1}$, wherein said oligomer is of not greater than about 5 kD and comprises at least 7 said heterocycles, where the pairing of heterocycles in relation to said target dsDNA is defined as Im/Py to G/C, Py/Im to C/G, and Py/Py to A/T and T/A and a pair of heterocycles refers to two heterocycles that are paired to a complementary pair of nucleotides in said dsDNA, and said heterocycles are linked by chains of 2 atoms, wherein at least some of the chains have NH,
said oligomer comprising at least two units of consecutive heterocycles which form intramolecular pairs,
said oligomer comprising an internal molecule γ-aminobutyric acid between said two units, and a unit of 6 N-heterocycles comprises an internal β-alanine, said internal β-alanine is paired with A and T,
said oligomer terminating, at one or both termini, in a glycine or β-alanine amino acid joined to an alkyl chain of from 2 to 4 carbon atoms comprising a polar group, and
where said oligomer has one or more hydrogen atoms away from the surface of said minor groove which may be substituted, wherein the total number of carbon atoms of substituents is not more than 30 carbon atoms.

18. A cell according to claim 17, wherein said polar group is a tertiary amine, with the proviso that only one terminus of an oligomer comprises said tertiary amine.

19. A cell according to claim 17, wherein said oligomer comprises at least 4 pairs of heterocycles.

20. A cell comprising dsDNA to which is bound in the minor groove at a target site a pair of oligomers of N-heterocycles consisting of N-methyl pyrrole (Py) and N-methyl imidazole (Im), where the oligomers are selected to provide specific binding to said dsDNA at said target site of a $K_a$ of not less than about $10^9$ $M^{-1}$, wherein each of said oligomers is of not greater than about 5 kD and comprises at least 6 said heterocycles, where the pairing of heterocycles in relation to said target dsDNA is defined as Im/Py to G/C, Py/Im to C/G, and Py/Py to A/T and T/A and a pair of heterocycles refers to two heterocycles that are paired to a complementary pair of nucleotides in said dsDNA, and said heterocycles are linked by chains of 2 atoms, wherein at least some of the chains have NH, each of said oligomers comprising at least one unit of 3 consecutive heterocycles which form intermolecular pairs with the other oligomer of the pair of oligomers, each of said oligomers comprises an internal β-alanine, said internal β-alanine is paired with an A or T;

each oligomer terminating, at one or both termini, in a glycine or β-alanine amino acid joined to an alkyl chain of from 2 to 4 carbon atoms comprising a polar group, and where each oligomer has one or more hydrogen atoms away from the surface of said minor groove which may be substituted, wherein the total number of carbon atoms of substituents is not more than 30 carbon atoms.

21. A cell according to claim 17, wherein said oligomer comprises an internal β-alanine dividing a sequence of 6 N-heterocycles and separated from said γ-aminobutyric acid by at least 2 heterocycles and said chains of 2 atoms are amido groups.

22. A method for reducing transcription of a gene in a cell, said method comprising:

bringing together a cell and oligomers selected to provide specific binding either singly or in pairs to dsDNA at a target site in the minor groove at said target site, each of said oligomers comprising organic cyclic groups of from 5 to 6 annular members, where at least 60% of the groups are heterocycles having from 1 to 3 heteroatoms, where the heteroatoms are nitrogen, oxygen and sulfur, and wherein at least 60% of the heterocycles have at least one nitrogen atom, and said heterocycles are linked by chains of 2 atoms, wherein at least some of the chains have NH, wherein at least one of said oligomers has at least 7 of said nitrogen containing heterocycles, where at least one of said heterocycles is specific for A, G, C or T, and a pair of heterocycles refers to two heterocycles paired to a complementary pair of nucleotides in said dsDNA, each oligomer comprising at least two units of 2 consecutive heterocycles which form, at the target sites, intramolecular pairs of heterocycles with itself or intermolecular pairs of heterocycles with another oligomer, where when an oligomer forms intramolecular pairs, said oligomer comprises an internal molecule which shifts the spacing of the heterocycles or forms a hairpin turn, and when two oligomers form intermolecular pairs, each oligomer comprises an internal aliphatic amino acid of from 2 to 6 carbon atoms, where said internal aliphatic amino acid is paired with an A or T; and each of said oligomers comprising at at least one terminus, an aliphatic amino acid of from 2 to 6 carbon atoms or an alkyl chain comprising a polar group 2 to 4 carbon atoms from the bond linking said alkyl chain to the remainder of each oligomer, where each oligomer has one or more hydrogen atoms away from the surface of said minor groove which may be substituted, wherein the total number of carbon atoms of substituents is not more than 100 carbon atoms;

whereby said oligomers bind to said target dsDNA and reduce the level of transcription.

23. A method according to claim 22, wherein said cell is a eukaryotic cell.

24. A method according to claim 23, wherein said eukaryotic cell is a mammalian cell.

25. A method according to claim 23, wherein said target dsDNA is viral dsDNA.

26. A method according to claim 22, wherein said cell is a prokaryotic cell.

27. A method according to claim 26, wherein said prokaryotic cell is a bacterial cell.

28. A method for reducing transcription of a gene in a cell, said method comprising:

bringing together said cell and oligomers of N-heterocycles consisting of N-methyl pyrrole (Py) and N-methyl imidazole (Im), where the oligomers are selected to provide specific binding either singly or in pairs to dsDNA in said cell in the minor groove of said dsDNA at a target site, wherein each of said oligomers comprises at least 6 said heterocycles, where the pairing of heterocycles in relation to said target dsDNA is defined as Im/Py to G/C, Py/Im to C/G, and Py/Py to A/T and T/A and a pair of heterocycles refers to two heterocycles that are paired to a complementary pair of nucleotides in said dsDNA, and said heterocycles are linked by chains of 2 atoms, wherein at least some of the chains have NH, each oligomer comprising at least two units of consecutive heterocycles which form, at target sites, intramolecular pairs of heterocycles with itself or intermolecular pairs of heterocycles with another oligomer, where when an oligomer forms intramolecular pairs, said oligomer comprises an internal molecule γ-aminobutyric acid, and when two oligomers form intermolecular pairs, each oligomer comprises an internal β-alanine, said internal β-alanine is paired with an A or T;

where each oligomer terminates, at one or both termini, in a glycine or β-alanine amino acid joined to an alkyl chain of from 2 to 4 carbon atoms comprising a polar group, with the proviso that a γ-aminobutyric acid may join the termini to circularize an oligomer, where each oligomer has one or more hydrogen atoms away from the surface of said minor groove which may be substituted, wherein the total number of carbon atoms of substituents is not more than 30 carbon atoms;

whereby said oligomers bind to said target dsDNA and reduce the level of transcription.

29. A method according to claim 28, wherein said chains of 2 atoms are amido groups.

30. A method according to claim 28, wherein one oligomer at target sites with two oligomers have one β-alanine separating units of at least 2 N-heterocycles.

31. A method according to claim 28, wherein said cell is a eukaryotic cell.

32. A method according to claim 31, wherein said eukaryotic cell is a mammalian cell.

33. A method according to claim 32, wherein said target dsDNA is viral dsDNA.

34. A method according to claim 28, wherein said cell is a prokaryotic cell.

35. A method according to claim 34, wherein said prokaryotic cell is a bacterial cell.

36. A method according to claim 28, wherein said oligomers bind to said target site with a $K_a$ of not less than about $10^9$ $M^{-1}$.

37. A method according to claim 28, wherein 2 oligomers which form intramolecular pairs or 4 oligomers which form two pairs of oligomers which form intermolecular pairs are employed for binding to two different target sites.

38. A method according to claim 28, wherein bonded to each oligomer is a chelated metal group.

39. A method according to claim 28, wherein said oligomer comprises at least 2 β-alanines.

40. A method for inhibiting proliferation of cells in a mammalian host, said method comprising:

administering a proliferation inhibiting amount of oligomers of N-heterocycles consisting of N-methyl pyrrole (Py) and N-methyl imidazole (Im), where the oligomers are selected to provide specific binding either singly or in pairs to dsDNA in the minor groove of said dsDNA at a target site, wherein each of said oligomers comprises at least 6 said heterocycles, where the pairing of heterocycles in relation to said target dsDNA is defined as Im/Py to G/C, Py/Im to C/G, and Py/Py to A/T and T/A and a pair of heterocycles refers to two heterocycles that are paired to a complementary pair of nucleotides in said dsDNA, and said heterocycles are linked by chains of 2 atoms, wherein at least some of the chains have NH, each oligomer comprising at least two units of consecutive heterocycles which form, at target sites, intramolecular pairs of heterocycles with itself or intermolecular pairs of heterocycles with another oligomer, where when an oligomer forms intramolecular pairs, said oligomer comprises an internal molecule γ-aminobutyric acid, and when two oligomers form intermolecular pairs, each oligomer comprises an internal β-alanine, said internal β-alanine is paired with an A or T;

where each oligomer terminates, at one or both termini, in a glycine or β-alanine amino acid joined to an alkyl chain of from 2 to 4 carbon atoms comprising a polar group, with the proviso that a γ-aminobutyric acid may join the termini to circularize an oligomer, where each oligomer has one or more hydrogen atoms away from the surface of said minor groove which may be substituted, wherein the total number of carbon atoms of substituents is not more than 30 carbon atoms, wherein said target dsDNA is a gene essential for proliferation of said cells; and said 1 to 2 oligomers bind to said target site, inhibiting transcription of said gene and reducing the proliferation of said cells.

41. A cell according to claim 20, wherein each oligomer comprises an internal β-alanine dividing a sequence of 6 N-heterocycles and said chains of 2 atoms are amido groups.

42. A cell according to claim 13, wherein said dsDNA comprises a viral gene comprising regulatory and coding regions containing one or more target sites with 1 to 2 oligomers bound in the minor groove.

43. A cell according to claim 13, wherein said dsDNA comprises a pathogenic gene comprising regulatory and coding regions containing one or more target sites with 1 to 2 oligomers bound in the minor groove.

44. A cell according to claim 13, wherein said dsDNA comprises a gene that is endogenous, exogenous, chromosomal, extra-chromosomal or non-integrated.

45. A cell according to claim 13, wherein said target site includes the nucleotide sequence 5'-AGTACT-3'.

46. A cell according to claim 13, wherein said oligomer is polyamide ImPyPyPy-γ-aminobutyric acid-ImPyPyPy-β-alanine-Dp, where Dp is dimethylaminopropylamide.

47. A method according to claim 23, wherein said eukaryotic cell is a plant cell.

48. A method according to claim 28, wherein one oligomer at target sites with two oligomers has one β-alanine separating units of at least 2 N-heterocycles.

49. A method according to claim 28, wherein said target site includes the nucleotide sequence 5'-AGTACT-3'.

50. A method according to claim 28, wherein said oligomer is polyamide ImPyPyPy-γ-aminobutyric acid-ImPyPyPy-β-alanine-Dp, where Dp is dimethylaminopropylamide.

51. A method according to claim 31, wherein said eukaryotic cell is a plant cell.

52. A method according to claim 40, wherein said target site includes the nucleotide sequence 5'-AGTACT-3'.

53. A method according to claim 40, wherein said oligomer is polyamide ImPyPyPy-γ-aminobutyric acid-ImPyPyPy-β-alanine-Dp, where Dp is dimethylaminopropylamide.

* * * * *